United States Patent [19]

Greenlee et al.

[11] Patent Number: 5,157,040
[45] Date of Patent: Oct. 20, 1992

[54] SUBSTITUTED QUINOLINES AS ANGIOTENSIN II ANTAGONISTS

[75] Inventors: William J. Greenlee, Teaneck; David B. R. Johnston, Warren; Malcolm MacCoss, Freehold, all of N.J.

[73] Assignee: Merck & Co., Inc., Rahway, N.J.

[21] Appl. No.: 681,216

[22] Filed: Apr. 5, 1991

[51] Int. Cl.⁵ .................. A61K 31/47; C07D 401/10
[52] U.S. Cl. .................. 514/312; 514/311; 514/314; 514/82; 514/230.8; 546/153; 546/168; 546/171; 546/23; 546/155; 546/156; 546/14; 544/97; 548/250
[58] Field of Search ............. 514/312, 311, 314, 82; 546/155, 153, 156, 23, 171, 168

[56] References Cited

U.S. PATENT DOCUMENTS

| | | | |
|---|---|---|---|
| 4,812,463 | 3/1989 | Graham et al. | 514/311 |
| 4,851,409 | 7/1989 | Young et al. | 546/156 |
| 4,868,193 | 9/1989 | Lee | 514/314 |
| 4,904,286 | 2/1990 | Musser et al. | 546/152 |
| 4,918,081 | 4/1990 | Huang et al. | 514/314 |
| 4,920,130 | 4/1990 | Huang et al. | 514/314 |
| 4,920,131 | 4/1990 | Huang et al. | 514/311 |
| 4,920,132 | 4/1990 | Huang et al. | 514/314 |
| 4,920,133 | 4/1990 | Huang et al. | 514/314 |
| 5,028,615 | 7/1991 | Huang et al. | 514/314 |
| 5,041,453 | 8/1991 | Huang et al. | 546/175 |
| 5,059,610 | 10/1991 | Huang et al. | 514/314 |
| 5,064,825 | 11/1991 | Chakrauarty et al. | 514/81 |
| 5,071,988 | 12/1991 | Failli | 546/172 |
| 5,084,462 | 1/1992 | Ackerman et al. | 514/312 |

FOREIGN PATENT DOCUMENTS 219308 4/1987
0326328 8/1989 European Pat. Off. .
411766 2/1991 European Pat. Off. .
419048 3/1991 European Pat. Off. .

*Primary Examiner*—Donald G. Daus
*Attorney, Agent, or Firm*—William H. Nicholson; Joseph F. DiPrima

[57] ABSTRACT

Substituted quinolines of the formula (I), are angiotensin II antagonists,

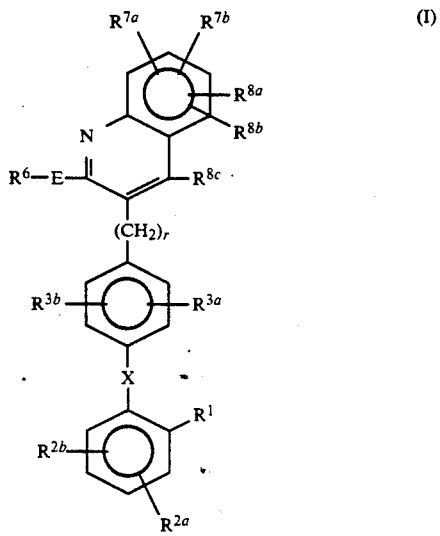

and useful in the treatment of hypertension, ocular hypertension and certain CNS disorders.

3 Claims, No Drawings

SUBSTITUTED QUINOLINES AS ANGIOTENSIN II ANTAGONISTS

INTRODUCTION OF THE INVENTION

This invention relates to novel substituted quinoline compounds and derivatives thereof which are useful as angiotensin II antagonists in the treatment of elevated blood pressure and congestive heart failure and in the treatment of ocular hypertension.

The compounds of this invention also have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia.

BACKGROUND OF THE INVENTION

Renin-angiotensin system (RAS) plays a central role in the regulation of normal blood pressure and seems to be critically involved in hypertension development and maintenance as well as congestive heart failure. Angiotensin II (AII), an octapeptide hormone is produced mainly in the blood during the cleavage of angiotensin I by angiotensin converting enzyme (ACE) localized on the endothelium of blood vessels of lung, kidney, and many other organs, and is the end product of the RAS. AII is a powerful arterial vasoconstricter that exerts its action by interacting with specific receptors present on cell membranes. One of the possible modes of controlling the RAS is angiotensin II receptor antagonism. Several peptide analogs of AII are known to inhibit the effect of this hormone by competitively blocking the receptors, but their experimental and clinical applications have been limited by their partial agonist activity and lack of oral absorption [M. Antonaccio. *Clin. Exp. Hypertens*, A4, 27–46 (1982); D. H. P. Streeten and G. H. Anderson, Jr.—*Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several non-peptide compounds have been described as AII antagonists. Illustrative of such compounds are those disclosed in U.S. Pat. Nos. 4,207,324; 4,340,598; 4,576,958; 4,582,847 and 4,880,804 in European Patent Applications 028,834; 245,637; 253,310; and 291,969; and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988), *Hypertension*, 13, 489–497 (1989)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

DETAILED DESCRIPTION OF THE INVENTION

The novel compounds of this invention have the general formula (I):

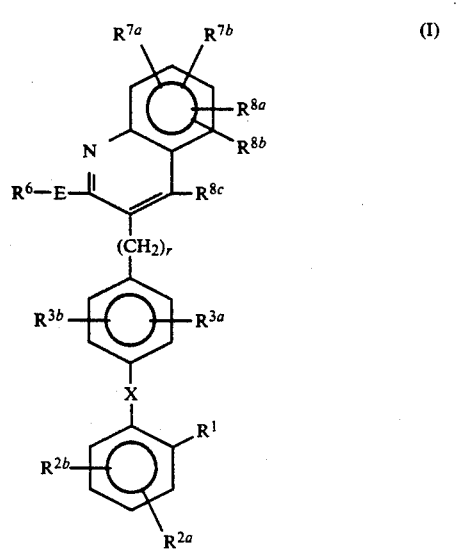

or a pharmaceutically acceptable salt thereof,
$R^1$ is
(a) —$CO_2R^4$,
(b) —$SO_3R^5$,
(c) —$NHSO_2CF_3$,
(d) —$PO(OR^5)_2$,
(e) —$SO_2$—NH—$R^9$,
(f) —$CONHOR^5$,
(g)

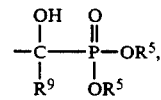

(h)

(i) —$SO_2NH$—heteroaryl,
(j) —$CH_2SO_2NH$—heteroaryl,
(k) —$SO_2NH$—CO—$R^{22}$,
(l) —$CH_2SO_2NH$—CO—$R^{22}$,
(m) —$CONH$—$SO_2R^{22}$,
(n) —$CH_2CONH$—$SO_2R^{22}$,
(o) —$NHSO_2NHCO$—$R^{22}$,
(p) —$NHCONHSO_2$—$R^{22}$,
(q) —$CH_2SO_2NH$—aryl,
(r) —$NHSO_2NHR^{22}$, (s) 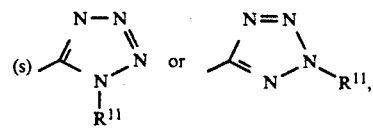

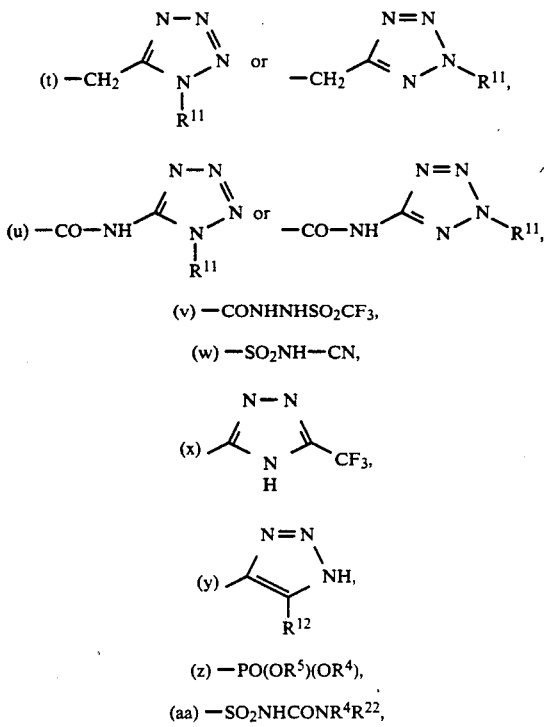

(v) —CONHNHSO$_2$CF$_3$, (w) —SO$_2$NH—CN, (z) —PO(OR$^5$)(OR$^4$), (aa) —SO$_2$NHCONR$^4$R$^{22}$, wherein heteroaryl is an unsubstituted, monosubstituted or disubstituted five or six membered aromatic ring comprising from 1 to 3 heteroatoms selected from the group consisting of O, N and S and wherein the substituents are members selected from the group consisting of —OH, —SH, —C$_1$-C$_4$-alkyl, —C$_1$-C$_4$-alkoxy, —CF$_3$, Cl, Br, F, I, —NO$_2$, —CO$_2$H, —CO$_2$—(C$_1$-C$_4$-alkyl), —NH$_2$, —NH(C$_1$-C$_4$-alkyl) and —N(C$_1$-C$_4$-alkyl)$_2$;

R$^{2a}$ and R$^{2b}$ are each independently
(a) H,
(b) Cl, Br, I, or F,
(c) NO$_2$,
(d) NH$_2$,
(e) C$_1$-C$_4$-alkylamino,
(f) di(C$_1$-C$_4$-alkyl)amino
(g) SO$_2$NHR$^9$,
(h) CF$_3$,
(i) C$_1$-C$_6$-alkyl,
(j) C$_1$-C$_6$-alkoxy,
(k) C$_1$-C$_6$-alkyl-S—,
(l) C$_2$-C$_6$-alkenyl,
(m) C$_2$-C$_6$-alkynyl;
(n) aryl,
(o) aryl(C$_1$-C$_4$-alkyl),
(p) C$_3$-C$_7$-cycloalkyl;

R$^{3a}$ is
(a) H,
(b) Cl, Br, I, or F,
(c) C$_1$-C$_6$-alkyl,
(d) C$_1$-C$_6$-alkoxy,
(e) C$_1$-C$_6$-alkoxyalkyl;

R$^{3b}$ is
.(a) H,
(b) Cl, Br, I, or F,
(c) NO$_2$,
(d) C$_1$-C$_6$-alkyl,
(e) C$_2$-C$_6$-alkanoyloxy,
(f) C$_3$-C$_7$-cycloalkyl,
(g) C$_1$-C$_6$-alkoxy,
(h) —NHSO$_2$R$^4$,
(i) hydroxy(C$_1$-C$_4$-alkyl),
(j) aryl(C$_1$-C$_4$-alkyl),
(k) C$_1$-C$_4$-alkylthio,
(l) C$_1$-C$_4$-alkyl sulfinyl,
(m) C$_1$-C$_4$-alkyl sulfonyl,
(n) NH$_2$,
(o) C$_1$-C$_4$-alkylamino,
(p) di(C$_1$-C$_4$-alkyl)amino,
(q) fluoro-C$_1$-C$_4$-alkyl—,
(r) —SO$_2$-NHR$^9$,
(s) aryl,
(t) furyl,
(u) CF$_3$,
(v) C$_2$-C$_6$-alkenyl,
(w) C$_2$-C$_6$-alkynyl;
wherein aryl is phenyl or naphthyl unsubstituted or substituted with one or two substituents selected from the group consisting of Cl, Br, I, F, N(R$^4$)$_2$, CO$_2$R$^4$, C$_1$-C$_4$-alkyl, C$_1$-C$_4$-alkoxy, NO$_2$, CF$_3$, C$_1$-C$_4$-alkylthio, and —OH;

R$^1$ is H, aryl or C$_1$-C$_6$ alkyl unsubstituted or substituted with aryl;

R$^{4a}$ is aryl or C$_1$-C$_6$-alkyl unsubstituted or substituted with, aryl;

R$^5$ is H, or

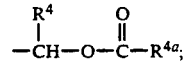

E is a single bond, —NR$^{13}$(CH$_2$)$_s$—, —S(O)$_x$(CH$_2$)$_s$— where x is 0 to 2 and s is 0 to 5, —CH(OH)—, —O—, or CO—;

R$^6$ is
(a) aryl unsubstituted or substituted with 1 or 2 substituents selected from the group consisting of Cl, Br, I, F, —O—C$_1$-C$_4$-alkyl, C$_1$-C$_4$-alkyl, —NO$_2$, —CF$_3$, —SO$_2$NR$^9$R$^{10}$, —S—C$_1$-C$_4$-alkyl, —OH, —NH$_2$, C$_3$-C$_7$-cycloalkyl, or C$_3$-C$_{10}$-alkenyl;
(b) C$_1$-C$_6$-alkyl, C$_2$-C$_5$-alkenyl or C$_2$-C$_5$-alkynyl each of which is unsubstituted or substituted with a substituent selected from the group consisting of aryl, C$_3$-C$_7$-cycloalkyl, Cl, Br, I, F, CF$_3$, CF$_2$CF$_3$, —NH$_2$, —NH(C$_1$-C$_4$-alkyl), —OR$^4$ —N(C$_1$-C$_4$-alkyl)$_2$, —NH—SO$_2$R$^4$, —COOR$^4$, or —SO$_2$NHR$^9$;
(c) an unsubstituted, monosubstituted or disubstituted heteroaromatic of 5 or 6 members comprising one or two heteroatoms selected from the group consisting of N, O, S, and wherein the substituents are members selected from the group consisting of —OH, —SH, C$_1$-C$_4$-alkyl, C$_1$-C$_4$-alkoxy, —CF$_3$, Cl, Br, I, F, or NO$_2$;
(d) C$_3$-C$_7$-cycloalkyl;
(e) perfluoro-C$_1$-C$_4$-alkyl,
(f) H;

R$^{7a}$ and R$^{7b}$ are independently
(a) H,
(b) C$_1$-C$_6$-alkyl, C$_2$-C$_6$-alkenyl or C$_2$-C$_6$-alkynyl,
(c) Cl, Br, I, F,
(d) CF$_3$, or
(e) when R$^{7a}$ and R$^{7b}$ are bonded to adjacent carbon atoms, they can be joined to form a benzo group;

R$^{8a}$ and R$^{8b}$ are independently
(a) H, (b) $C_1$-$C_6$-alkyl unsubstituted or substituted with a substituent selected from the group consisting of —OH, -guanidino, $C_1$-$C_4$-alkoxy, —N($R^4$)$_2$, COOR$^4$, —CON($R^4$)$_2$, —O—COR$^4$, -aryl, -heteroaryl, —S(O)$_x$-$R^{22}$, -tetrazol-5-yl, —CONHSO$_2$R$^{22}$, —SO$_2$NH-heteroaryl, —SO$_2$NHCOR$^{22}$, —PO(OR$^4$)$_2$, —PO(OR$^4$)R$^9$, —SO$_2$NH—CN, —NR$^{10}$COOR$^{22}$,
(c) —CO-aryl,
(d) —$C_3$-$C_7$-cycloalkyl,
(e) Cl, Br, I, F,
(f) —OH,
(g) —OR$^{22}$,
(h) —$C_1$-$C_4$-perfluoroalkyl,
(i) —S(O)$_x$-$R^{22}$,
(j) —COOR$^4$,
(k) —SO$_3$H,
(l) —NR$^4$R$^{22}$,
(m) —NR$^4$COR$^{22}$,
(n) —NR$^4$COOR$^{22}$,
(o) —SO$_2$NR$^9$R$^{10}$,
(p) —NO$_2$,
(q) —N(R$^4$)SO$_2$R$^{22}$,
(r) —NR$^4$CONR$^4$R$^{22}$,
(s)

(t) -aryl or -heteroaryl,
(u) —NHSO$_2$CF$_3$,
(v) —SO$_2$NH-heteroaryl,
(w) —SO$_2$NHCOR$^{22}$,
(x) —CONHSO$_2$R$^{22}$,
(y) —PO(OR$^4$)$_2$,
(z) —PO(OR$^4$)R$^9$,
(aa) -tetrazol-5-yl,
(bb) —CONH(tetrazol-5-yl),
(cc) —COR$^4$,
(dd) —SO$_2$NHCN
(ee)

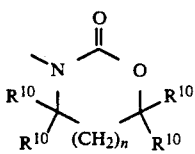

where n=0 or 1.
$R^{8c}$ is
(a) —CH$_2$CO$_2$R$^{4b}$ wherein R$^{4b}$ is R$^4$ or

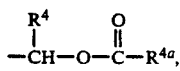

(b) —CO$_2$R$^{4b}$,
(c) —CH$_2$OH,
(d) —CH$_2$OCOR$^9$,
(e) —CH$_2$PO(OR$^4$)$_2$,
(f) —CH$_2$PO(OR$^4$)R$^9$,
(g) —CH$_2$S(O)$_x$R$^{22}$,
(h) —S(O)$_x$R$^{22}$,
(i) —CONR$^4$R$^{22}$,
(j) —CONHSO$_2$R$^{22}$,
(k) —CH$_2$SO$_2$NHCOR$^{22}$,
(l) —SO$_2$NHCOR$^{22}$,
(m) —SO$_2$NH-heteroaryl,
(n) —CH$_2$SO$_2$NR$^4$R$^{22}$,
(o) —SO$_2$NR$^4$R$^{22}$,
(p) —CH$_2$(tetrazol-5-yl),
(q) —PO(OR$^4$)$_2$,
(r) —PO(OR$^4$)R$^9$,
(s) —N(R$^4$)$_2$,
(t) —NHSO$_2$CF$_3$,
(u) -tetrazol-5-yl;
$R^9$ is H, $C_1$-$C_5$-alkyl, aryl or arylmethyl;
$R^{10}$ is H, $C_1$-$C_4$-alkyl;
$R^{11}$ is H, $C_1$-$C_6$alkyl, $C_1$-$C_4$-alkenyl, $C_1$-$C_4$-alkoxy alkyl, or

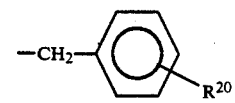

$R^{12}$ is —CN, —NO$_2$ or —CO$_2$R$^4$;
$R^{13}$ is H, ($C_1$-$C_4$-alkyl)CO—, $C_1$-$C_6$-alkyl, allyl, $C_3$-$C_6$-cycloalkyl, aryl or arylmethyl;
$R^{14}$ is H, $C_1$-$C_8$-alkyl, $C_1$-$C_8$-perfluoroalkyl, $C_3$-$C_6$-cycloalkyl, aryl or arylmethyl;
$R^{15}$ is H, $C_1$-$C_6$-alkyl;
$R^{16}$ is H, $C_1$-$C_6$-alkyl, $C_3$-$C_6$-cycloalkyl, aryl or arylmethyl;
$R^{17}$ is —NR$^9$R$^{10}$, —OR$^{10}$, —NHCONH$_2$, —NHCSNH$_2$,

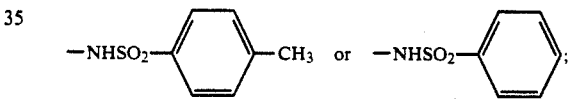

$R^{18}$ and $R^{19}$ are independently $C_1$-$C_4$-alkyl or taken together are —(CH$_2$)$_q$— where q is 2 or 3;
$R^{20}$ is H, —NO$_2$, —NH$_2$, —OH or —OCH$_3$;
$R^{22}$ is
(a) aryl,
(b) heteroaryl,
(c) $C_3$-$C_7$-cycloalkyl,
(d) $C_1$-$C_6$-alkyl unsubstituted or substituted with a substituent selected from the group consisting of aryl, heteroaryl, —OH, —SH, $C_1$-$C_4$-alkyl, —O($C_1$-$C_4$-alkyl), —S($C_1$-$C_4$-alkyl), —CF$_3$, Cl, Br, F, I, —NO$_2$, —CO$_2$H, CO$_2$—$C_1$-$C_4$-alkyl, —NH$_2$, —NH($C_1$-$C_4$-alkyl), —N($C_1$-$C_4$-alkyl)$_2$, —PO$_3$H$_2$, —PO(OH)(O—$C_1$-$C_4$-alkyl), —PO(OR$^4$)R$^9$;
(e) perfluoro-$C_1$-$C_4$-alkyl;
X is
(a) a carbon-carbon single bond,
(b) —CO—,
(c) —O—,
(d) —S—,
(e)

(f)

(g)

(h) —OCH₂—,
(i) —CH₂O—
(j) —SCH₂—,
(k) —CH₂S—,
(l) —NHC(R⁹)(R¹⁰),
(m) —NR⁹SO₂—,
(n) —SO₂NR⁹—,
(o) —C(R⁹)(R¹⁰) NH—,
(p) —CH=CH—,
(q) —CF=CF—,
(r) —CH=CF—,
(s) —CF=CH—,
(t) —CH₂CH₂—,
(u) —CF₂CF₂—,

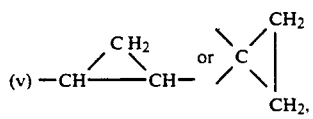

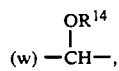

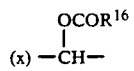

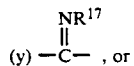

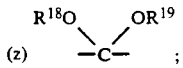

r is 1 or 2.

One embodiment of the compounds of formula (I) are those compounds wherein:

R¹ is
(a) —CO₂R⁴,
(b) —SO₂NH-heteroaryl,
(c) —SO₂NH—CO—R²²,
(d) —CH₂SO₂NH—CO—R²²,
(e) —CONH—SO₂R²²,
(f) —CH₂CONH—SO₂R²²,
(g) —NHSO₂NHCO—R²²,
(h) —NHCONHSO₂—R²²,

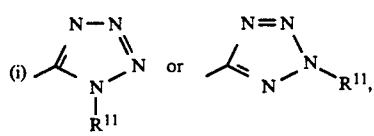

(j) —SO₂NH—CN,
(k) —SO₂NHCONR⁴R²²,

R⁶ is $C_1$-$C_6$-alkyl, $C_2$-$C_5$-alkenyl or $C_2$-$C_5$-alkynyl each of which is unsubstituted or substituted with a substituent selected from the group consisting of aryl, $C_3$-$C_7$-cycloalkyl, Cl, Br, I, F, $CF_3$, —$CF_2CF_3$, —$NH_2$, —NH($C_1$-$C_4$-alkyl), —$OR^4$ —N($C_1$-$C_4$-alkyl)₂, —NH—$SO_2R^4$, —$COOR^4$, —$SO_2NHR^9$; and, X is
(a) a carbon-carbon single bond,
(b) —CO—,
(c) —O—,
(d) —S—,
(e)

Preferred compounds of the invention are those that are members of the following group:

(1) 2-Butyl-4-carboxy-3-[(2'-carboxybiphen-4-yl)methyl]quinoline;
(2) 4-Carboxy-3-[(2'-carboxybiphen-4-yl)methyl]-2-propylquinoline;
(3) 4-Carboxy-3-[(2'-carboxybiphen-4-yl)methyl]-2-ethylquinoline;
(4) 4-Carboxy-3-[(2'-carboxybiphen-4-yl)methyl]-2-isopropylquinoline;
(5) 4-Carboxy-3-[(2'-carboxybiphen-4-yl)methyl]-2-cyclopropylquinoline;
(6) 4-Carboxy-3-[(2'-carboxybiphen-4-yl)methyl]-6-methyl-2-propylquinoline;
(7) 4-Carboxy-3-[(2'-carboxybiphen-4-yl)methyl]-6-isopropyl-2-propylquinoline;
(8) 4-Carboxy-3-[(2'-carbomethoxybiphen-4-yl)methyl]-6-methyl-2-propylquinoline;
(9) 4-Carboxy-3-[(2'-carboxybiphen-4-yl)methyl]-5-methylquinoline;
(10) 4-Carboxy-3-[(2'-carboxybiphen-4-yl)methyl]-2-butyl-6-(N-methyl-N-isopropyloxycarbonyl)-aminoquinoline;
(11) 4-Carboxy-3-[(2'-carboxybiphen-4-yl)methyl]-6-(N-methyl)amino-2-propylquinoline;
(12) 4-Carboxy-3-[(2'-carboxybiphen-4-yl)methyl]-2-cyclopropyl-6-methylsulfinylquinoline;
(13) 4-Carboxy-3-[(2'-carboxybiphen-4-yl)methyl]-2-ethyl-6-methylsulfonylquinoline;
(14) 4-Carboxy-3-[(2'-carboxybiphen-4-yl)methyl]-6-(N-methyl-N-isobutylcarbonyl)amino-2-propylquinoline;
(15) 4-Carboxy-3-[(2'-carboxybiphen-4-yl)methyl]-2-ethyl-6-nitroquinoline;
(16) 4-Carboxy-3-[(2'-carboxybiphen-4-yl)methyl]-2-ethyl-5-hydroxymethylquinoline;
(17) 4-Carboxy-3-[(2'-carboxybiphen-4-yl)methyl]-2-ethyl-5-ethylquinoline;
(18) 4-Carboxy-3-[(2'-carboxybiphen-4-yl)methyl]-2-propyl-6-trifluoromethylquinoline;
(19) 4-Carboxy-3-[(2'-carboxybiphen-4-yl)methyl]-2-ethyl-6-fluoroquinoline;
(20) 3-[(2'-Carboxybiphen-4-yl)methyl]-4-hydroxymethyl-2-propyl-6-methylquinoline;
(21) 4-Carboxy-3-[(2'-carboxybiphen-4-yl)methyl]-2-ethyl-6-methylquinoline;
(22) 4-Carboethoxy-3-[(2'-carboxybiphen-4-yl)-methyl]-2-ethyl-5-methylquinoline;
(23) 4-Carboxymethyl-3-[(2'-carboxybiphen-4-yl)methyl]-2-propyl-6-methylquinoline;

(24) 3-[(2′-Carboxybiphen-4-yl)methyl]-6-methyl-4-(N-methylsulfonyl)carboxamido-2-propylquinoline;
(25) 3-[(2′-Carboxybiphen-4-yl)methyl]-6-methyl-4-(N-phenylsulfonyl)carboxamido-2-propylquinoline;
(26) 3-[(2′-Carboxybiphen-4-yl)methyl]-6-methyl-2-propyl-4-trifluoromethanesulfonamidoquinoline;
(27) 3-[(2′-Carboxybiphen-4-yl)methyl]-6-methyl-2-propyl-4-(N-pyridin-2-yl)sulfonamidoquinoline;
(28) 2-Butyl-4-carboxy-3-[(2′-(tetrazol-5-yl)biphen-4-yl)methyl]quinoline;
(29) 4-Carboxy-2-propyl-3-[(2′-(tetrazol-5-yl)-biphen-4-yl)methyl]quinoline;
(30) 4-Carboxy-2-ethyl-3-[(2′-(tetrazol-5-yl)-biphen-4-yl)methyl]quinoline;
(31) 4-Carboxy-2-isopropyl-3-[(2′-(tetrazol-5-yl)-biphen-4-yl)methyl]quinoline;
(32) 4-Carboxy-2-cyclopropyl-6-methyl-3-[(2′-(tetrazol-5-yl)biphen-4-yl)methyl]quinoline;
(33) 4-Carboxy-6-methyl-2-propyl-3-[(2′-(tetrazol-5-yl)biphen-4-yl)methyl]quinoline;
(34) 4-Carboxy-6-isopropyl-2-propyl-3-[(2′-(tetrazol-5-yl)biphen-4-yl)methyl]quinoline;
(35) 4-Carboxy-6-methyl-2-propyl-3-[(2′-(tetrazol-5-yl)biphen-4-yl)methyl]quinoline;
(36) 4-Carboxy-5-methyl-3-[(2′-(tetrazol-5-yl)-biphen-4-yl)methyl]quinoline;
(37) 2-Butyl-4-carboxy-6-(N-methyl-N-isopropyloxycarbonyl)amino-3-[(2′-(tetrazol-5-yl)biphen-4-yl)methyl]quinoline;
(38) 4-Carboxy-6-(N-methyl)amino-2-propyl-3-[(2′-(tetrazol-5-yl)biphen-4-yl)methyl]quinoline;
(39) 4-Carboxy-2-cyclopropyl-6-methylsulfinyl-3-[(2′-(tetrazol-5-yl)biphen-4-yl)methyl]-quinoline;
(40) 4-Carboxy-2-ethyl-6-methylsulfonyl-3-[(2′-(tetrazol-5-yl)biphen-4-yl)methyl]quinoline;
(41) 4-Carboxy-6-(N-methyl-N-isobutyloxycarbonyl)-amino-2-propyl-3-[(2′-(tetrazol-5-yl)biphen-4-yl)methyl]quinoline;
(42) 4-Carboxy-2-propyl-6-nitro-3-[(2′-(tetrazol-5-yl)biphen-4-yl)methyl]quinoline;
(43) 4-Carboxy-2-ethyl-5-hydroxymethyl-3-[(2′-(tetrazol-5-yl)biphen-4-yl)methyl]quinoline;
(44) 4-Carboxy-2-ethyl-5-ethyl-3-[(2′-(tetrazol-5-yl)biphen-4-yl)methyl]quinoline;
(45) 4-Carboxy-2-propyl-3-[(2′-(tetrazol-5-yl)-biphen-4-yl)methyl]-6-trifluoromethylquinoline;
(46) 4-Carboxy-2-ethyl-6-fluoro-3-[(2′-(tetrazol-5-yl)biphen-4-yl)methyl]quinoline;
(47) 4-Hydroxymethyl-6-methyl-2-propyl-3-[(2′-(tetrazol-5-yl)biphen-4-yl)methyl]quinoline;
(48) 4-Carbomethoxy-2-propyl-6-methyl-3-[(2′-tetrazol-5-yl)biphen-4-yl)methyl]quinoline;
(49) 4-Carboethoxy-2-ethyl-5-methyl-3-[(2′-(tetrazol-5-yl)biphen-4-yl)methyl]quinoline;
(50) 4-Carboxymethyl-6-methyl-2-propyl-3-[(2′-(tetrazol-5-yl)biphen-4-yl)methyl]quinoline;
(51) 6-Methyl-4-(N-methylsulfonyl)carboxamido-2-propyl-3-[(2′-(tetrazol-5-yl)biphen-4-yl)-methyl]quinoline;
(52) 6-Methyl-4-(N-phenylsulfonyl)carboxamido-2-propyl-3-[(2′-(tetrazol-5-yl)biphen-4-yl)-methyl]quinoline;
(53) 6-Methyl-2-propyl-4-trifluoromethanesulfonamido-3-[(2′-(tetrazol-5-yl)biphen-4-yl)-methyl]quinoline;
(54) 6-Methyl-2-propyl-4-(N-pyridin-2-yl)sulfonamido-3-[(2′-(tetrazol-5-yl)biphen-4-yl)-methyl]quinoline;
(55) 2-Butyl-4-carboxy-6-methyl-3-[(N-methylsulfonyl)carboxamidobiphen-4-yl)methyl]quinoline;
(56) 2-Butyl-4-carboxy-6-methyl-3-[(N-phenylsulfonyl)carboxamidobiphen-4-yl)methyl]quinoline;
(57) 2-Butyl-4-carboxy-3-[(N-(4-chloro)phenylsulfonyl)carboxamidobiphen-4-yl)methyl]-6-methylquinoline;
(58) 3-[(N-Acetyl)sulfonamidobiphen-4-yl)methyl]-2-butyl-4-carboxy-6-methyl-quinoline;
(59) 2-Butyl-4-carboxy-6-methyl-3-](N-trifluoroacetyl)-sulfonamidobiphen-4-yl)methyl]quinoline;
(60) 2-Butyl-4-carboxy-3-[(N-isobutanoyl)sulfonamidobipen-4-yl)methyl]-6-methylquinoline;
(61) 2-Butyl-4-carboxy-6-methyl-3-[(N-pivaloyl)-sulfonamidobiphen-4-yl)methyl]quinoline;
(62) 2-Butyl-4-carboxy-6-methyl-3-[(N-pyrimidin-2-yl)sulfonamidobiphen-4-yl)methyl]quinoline;
(63) 2-Butyl-4-carboxy-6-methyl-3-[(N-pyrimidin-2-yl)sulfonamidobiphen-4-yl)methyl]quinoline;

The compounds of this invention were prepared, as illustrated in Scheme 1, by the condensation of an appropriately substituted isatin (i) with an appropriately substituted ketone (ii) using the conditions of the Pfitzinger reaction (heating with KOH/H2O/EtOH). In some cases, the conditions described in U.S. Pat. No. 4,680,299 (stirring with Et3N, followed by heating in aqueous acid) give superior results. Where the ketone employed has a methylene group on both sides of the carbonyl, two cinchoninic acids (iii and iv) may be formed.

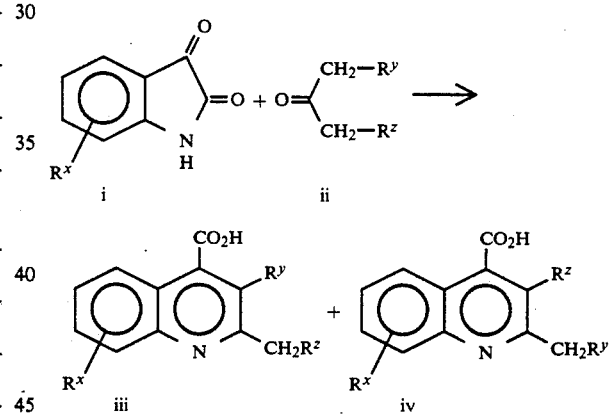

$R^x$ = The collective group of $R^{7a}$, $R^{7b}$, $R^{8a}$ and $R^{8b}$ as defined in Formula (I).

$R^y$ =

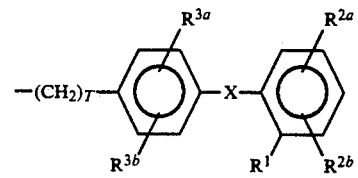

T = 0 or 1
$R^z = R^6$ as defined in Formula (I).

It will be obvious to those skilled in the art that in some instances the substituents as defined above will be inappropriate, e.g., due to instability under the condensation reaction conditions. In these instances, $R^x$, $R^y$, and $R^z$ are taken to mean groups which will survive the condensation reaction conditions but subsequently be convertable to the corresponding groups as defined above.

In contrast, when the ketone has only a single adjacent methylene, (e.g., cyclopropyl ketone (v) only one isomer (vi) is obtained as illustrated in Scheme 2.

SCHEME 2

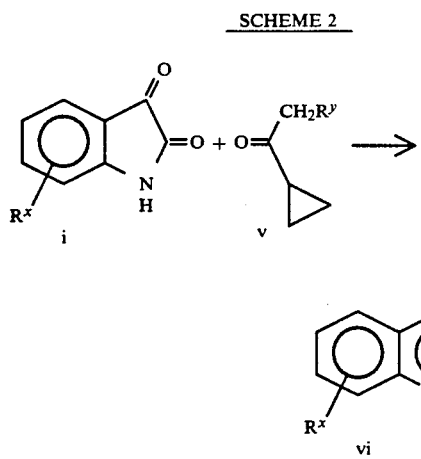

In some cases, the mix of cinchoninic acids needs only to be separated to give the desired product while in others, the separated acid or derivative is further elaborated to give the final product.

The ketones used in the condensation are prepared from an appropriate β-ketoester, followed by saponification/decarboxylation. While a few of the necessary ketoesters are available commercially, in many instances they must be prepared.

The reaction sequence is illustrated by the preparation of 4-(3-oxooctyl)-2'-(tetrazol-5-yl)-biphenyl (3), shown in Scheme 3.

SCHEME 3

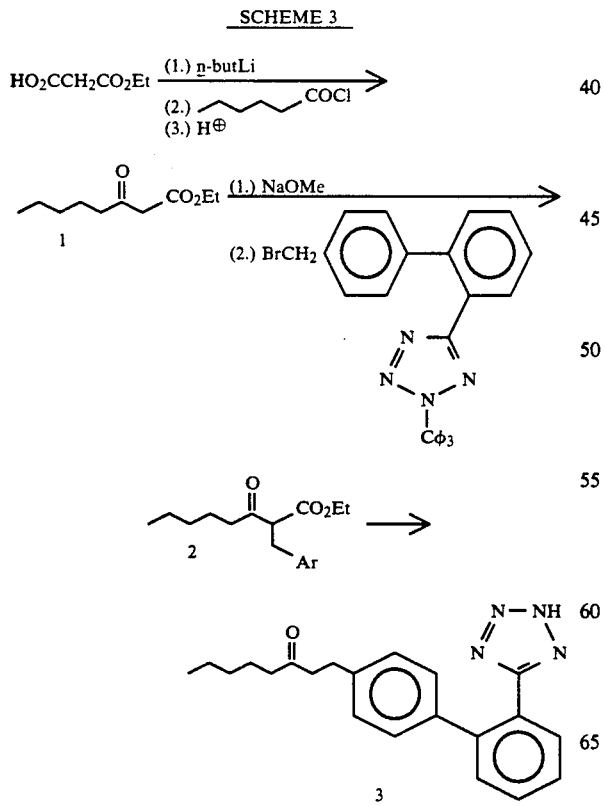

Here, the dianion of the malonate monoester is acylated with an acid chloride. The intermediate, after acidification, decarboxylates to give 1. Alkylation of the anion of 1 with the arylmethyl halide shown affords 2. While saponification/decarboxylation conditions generally give 3, the trityl group will sometimes partially survive. Since tritylated tetrazolyl ketones have generally given poorer results in the subsequent condensation than the free tetrazol ketones, it is desirable in these instances to deliberately complete its removal with a further acid treatment.

Preparation of a typical cinchoninic acid is illustrated in Scheme 4 where 4-carboxy-6-methyl-2-pentyl-3-[[2'-(5-tetrazolyl)biphenyl-4-yl]methyl]-quinoline (4) is obtained.

SCHEME 4

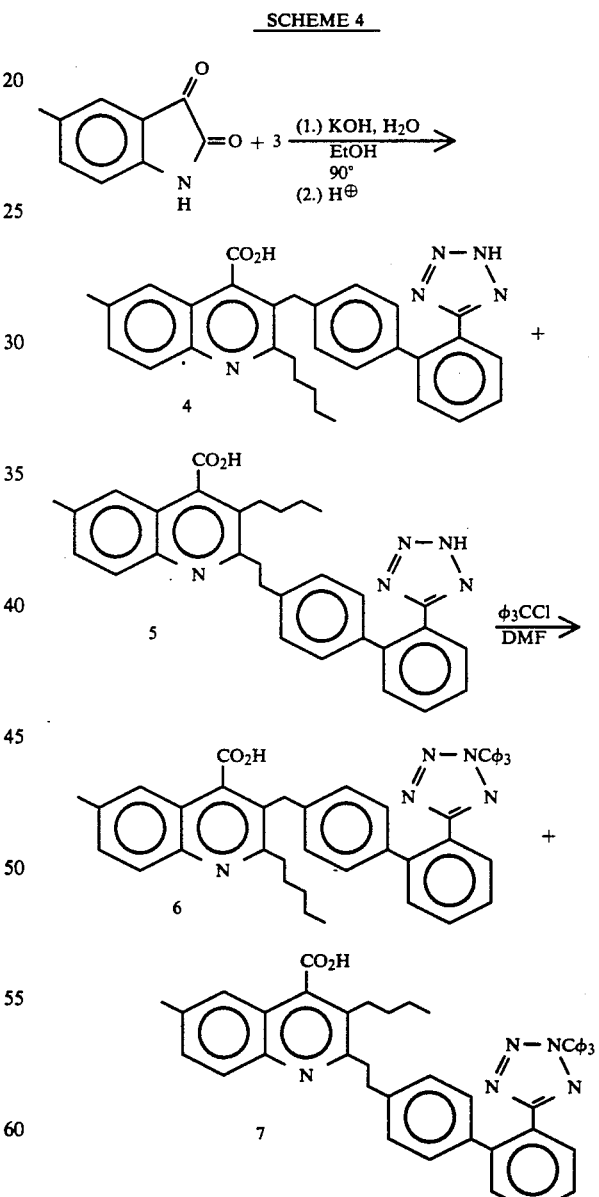

As shown in Scheme 4, ketone 3 is heated with 5-methylisatin in H$_2$O/KOH/EtOH at ~95° C. for 5-8 days. Upon workup, a mixture of crude 4 and 5 is obtained. These are most conveniently separated by preparative thin layer chromatography (tlc), after tritylation, to 6 and 7, in which form they are cleanly resolved. Pure 6 is then deblocked by heating in HOAc/H2O to give pure 4. Alternatively, 6 may now be further modified, as illustrated in Scheme 5.

Treatment of 6 with diazomethane gives ester 8 which can be deblocked with heating in HOAc/H2O to give the ester of 4 (10), or futher modified, e.g. by reduction with LiAlH4 to the hydroxymethyl compound 9 which upon heating in HOAc/H2O gives 11.

meric cinchoninic acids are separated as their esters. Scheme 6 illustrates such a route.

Ketone 12, prepared analogously to 3 (Scheme 3), is condensed with the isatin shown as in Scheme 4. In this example, the mixture of cinchoninic acids is esterified with diazomethanes and separated by a mixture of chromatography and fractional crystallization. Aryl coupling with the blocked aryl tetrazole 18 is then effected by lithiation of 15 with t-butyllithium, conversion to the aryl zinc with $ZnCl_2$, and, finally, coupling with 18 in

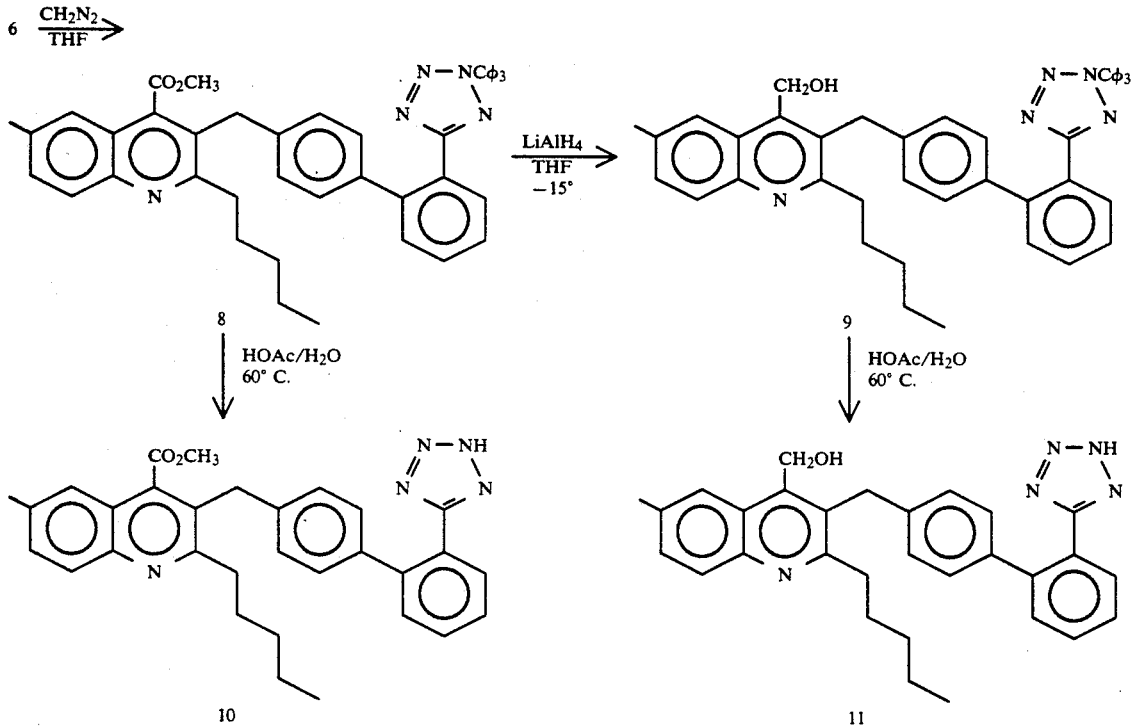

In an alternate route, the initially prepared cinchoninic acids contain a single aryl ring on the side chain which is subsequently elaborated. In this case, the isothe presence of $Ni(P\phi_3)_2Cl_2$. After isolation, the ester 16a is deblocked with HOAc/H2O and saponified to 4.

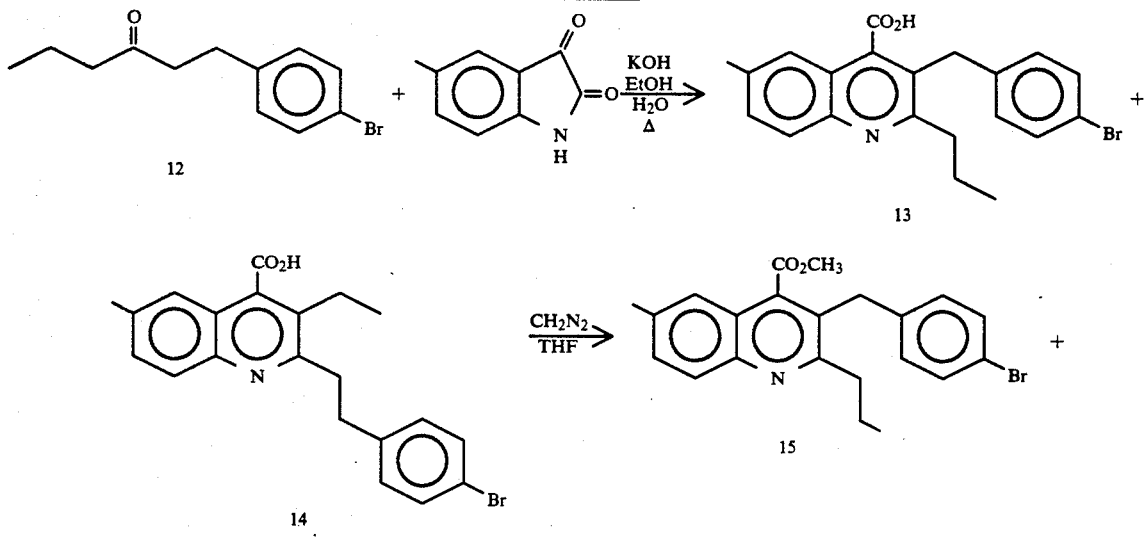

-continued
SCHEME 6
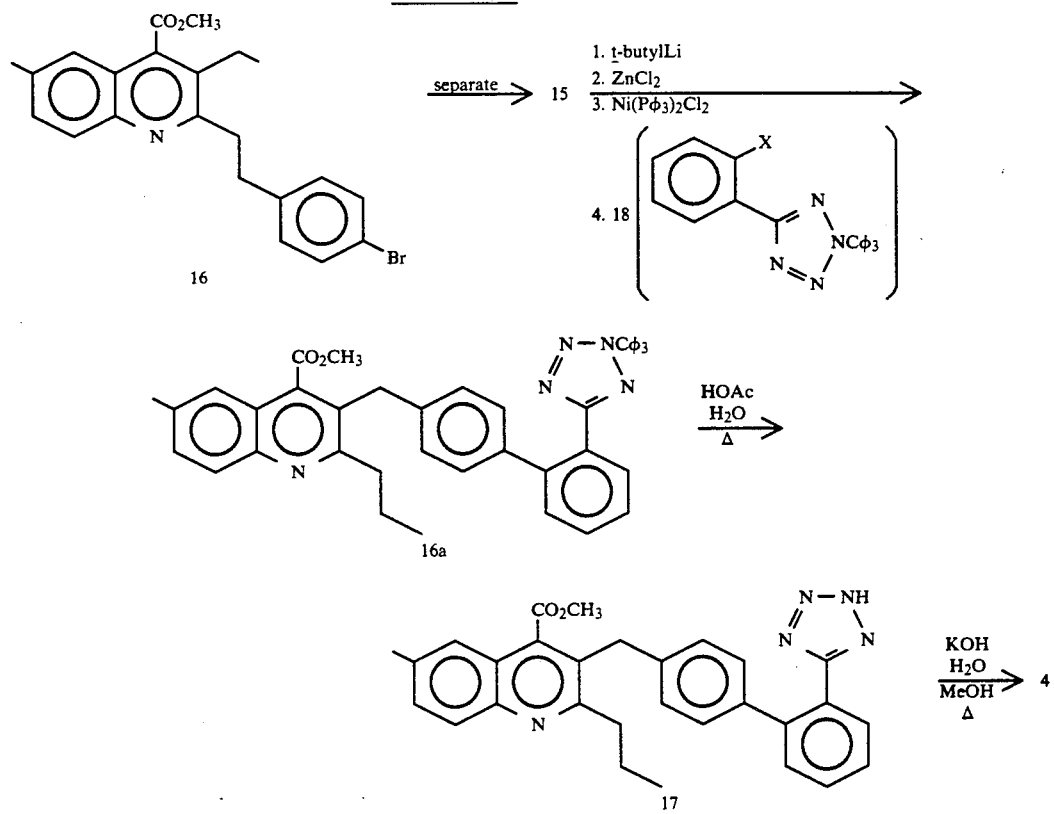
Compound 18 was obtained by the method described in Example 44 Step B.
Another example of the biaryl coupling reaction is illustrated by the alternate preparation of the bisnor analog of 11 shown in Scheme 6a.
SCHEME 6A
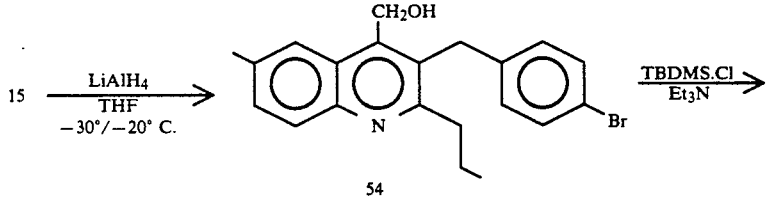
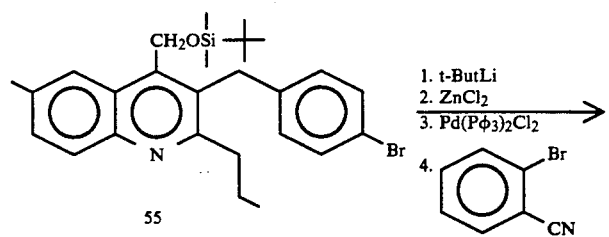
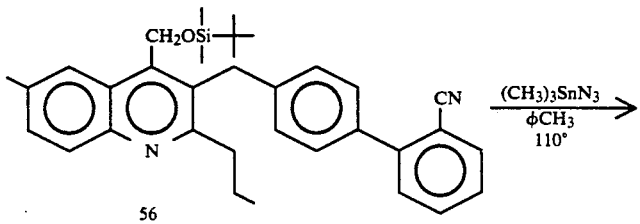

SCHEME 6A

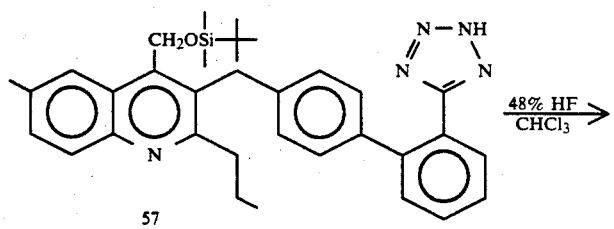

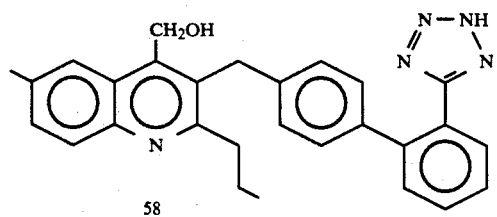

Ester 15 is reduced with LiAlH$_4$ and converted to its t-butyldimethylsilyl ether (55); this is coupled with 2-bromobenzonitrile as a Scheme 6A to give 56. Conversion of the nitrile to the tetrazole by heating with excess trimethyltin azide gives 57 which upon deblocking with 48% HF/CHCl$_3$ gives the desired product (58).

SCHEME 7

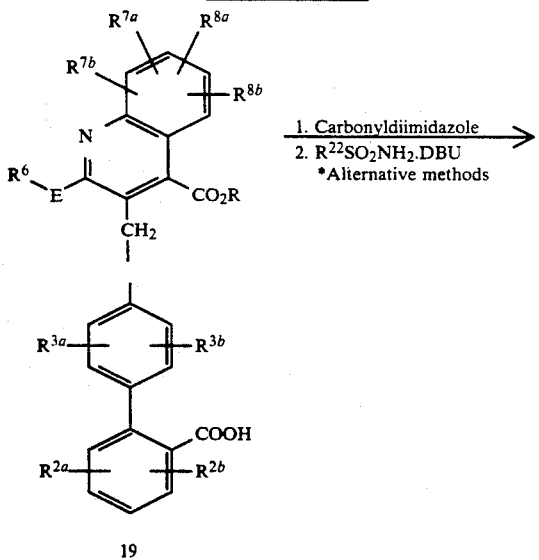

-continued
SCHEME 7

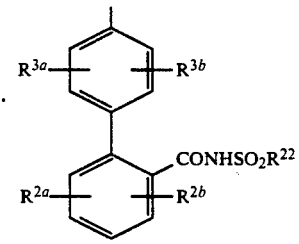

R = C(CH$_3$)$_3$ or CH$_2$φ

*Alternative Methods:
a) (i) SOCl$_2$, reflux
   (ii) R$^{22}$SO$_2$NH$^-$M$^+$ (where M is Na or Li)
b) (i) (COCl)$_2$—DMF, −20° C.
   (ii) R$^{22}$SO$_2$NH$^-$M$^+$ Another example of biaryl coupling is illustrated in Scheme 8, here used to prepare biarylsulfonamides. A 4-bromobenzylated cinchoninate, 32, is converted to the aryltin Scheme 7 illustrates some typical routes by which a carboxylic acid functionality, in this case in the biphenyl side chain, may be converted to an acylsulfonamide group. The same strategy may be used in those instances where the carboxylic acid functionality is in the quinoline system, typically at C$_4$. The preparation of 19 can be readily achieved by the method illustrated in Scheme 6A. In the present case 55 would bear e.g., a carbobenzyloxy group at C$_4$ in place of the silyloxymethyl group, and the nitrile of the coupling substrate bromobenzonitrile would be replaced with, e.g., a carbo-t-butoxy group. After coupling, the product, corresponding to 57 would be the t-butyl ester of 19. Following selective acid deblocking, 19 itself would be available for the Scheme 7 transformation to 20; hydrogenolytic deblocking of the 4-carboxyl would give the products of the invention. It should be obvious to those skilled in the art that if the blocking groups were reversed, the resultant 19 diester would bear the t-butyl ester at the 4-position of the quinoline and the benzyl ester on the biphenyl side chain. Selective acid deblocking would

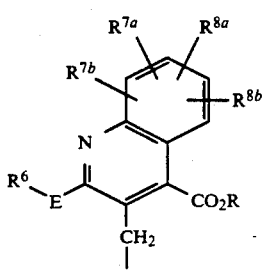

then allow transformations at the 4-carboxylic acid position and by obvious subsequent steps to another group of products of this invention. A further alternative available lies in reversing the order of deblocking conditions thus allowing a choice from a single diester as to which carboxylic functionality will be modified. derivative 31. Coupling with an appropriate bromoarylsulfonamide to give 20 or 30, depending on the nature of the blocking group $R^Q$. Deblocking, in this example with e.g. HF or TFA, affords the final product. It should be obvious that a wide variety of bromoaryl groups substituted with alternate, i.e., non-sulfonamide groups, could be used in such a coupling.

The biaryl sulfonamides 29 and 30 can be prepared using palladium(O) catalyzed cross-coupling reactions of appropriate aryl-organotin precursors [J. K. Stille, *Pure Appl. Chem.*, 57, 1771 (1985); T. R. Baiely, *Tetrahedron Lett.*, 27, 4407 (1986); D. A. Widdowson and Y. Z. Zhang, *Tetrahedron*, 42, 2111 (1986)], as outlined in Scheme 10. The organotin compound 31 [S. M. Moerlein, *J. Organometallic Chem.*, 319, 29 (1987)], obtained from the aromatic precursor 32, may be coupled with aryl sulfonamide 33 and 34 using Pd(PPh$_3$)$_4$ or (PPh$_3$)$_2$PdCl$_2$ as catalysts to give biaryl sulfonamide 29 and 30.

SCHEME 8

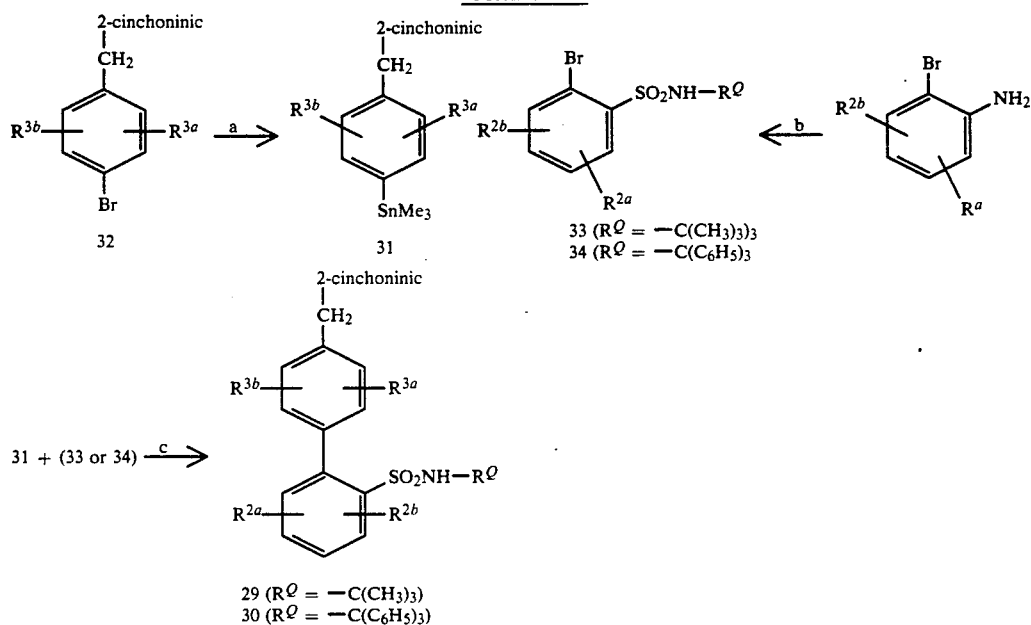

a. (i) t-BuLi/ether, −78° C.
   (ii) Me$_3$SnCl
b. (i) NaNO$_2$/HCl
   (ii) SO$_2$, CuCl$_2$
c. Pd(PPh$_3$)$_4$, Toluene, reflux or (PPh$_3$)$_2$PdCl$_2$, DMF, 90° C.

SCHEME 9

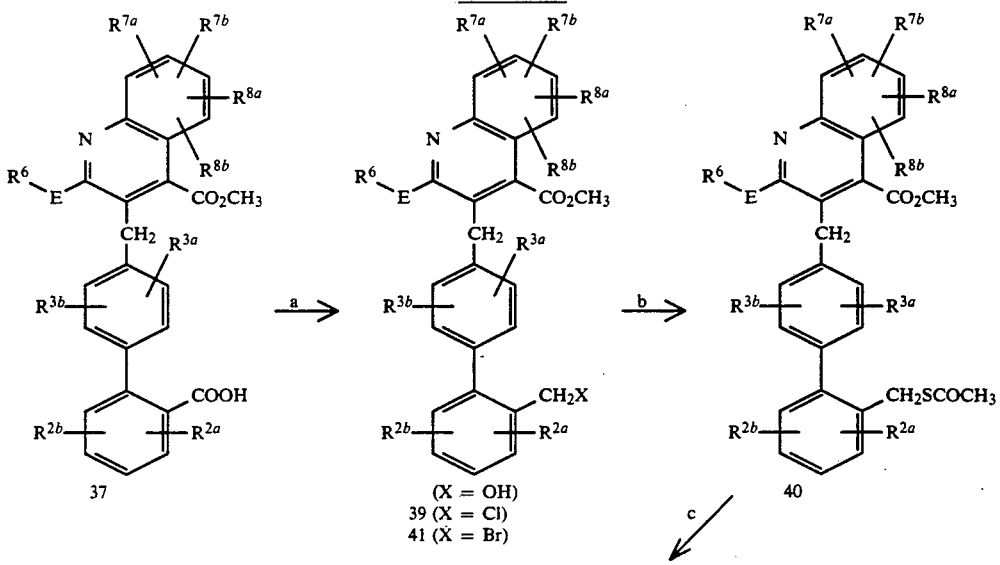

SCHEME 9
-continued

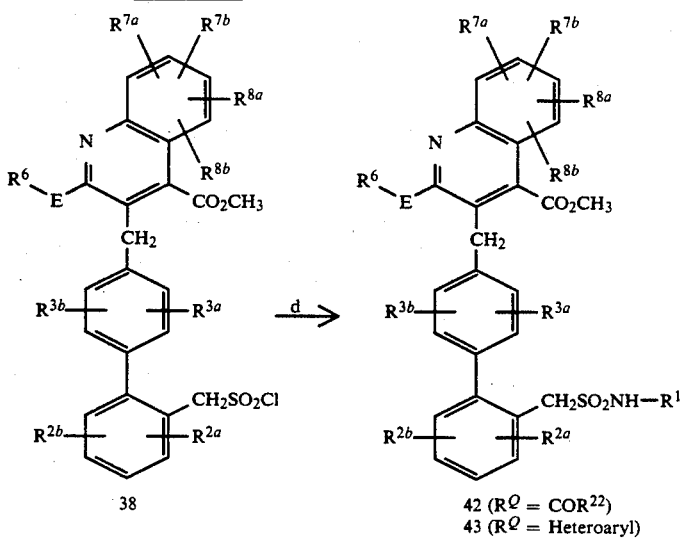

a. (i) EtOCOCl/Et$_3$N, THF, 0° C
   (ii) NaBH$_4$
   (iii) CCl$_4$ or CBr$_4$/PPh$_3$
b. AcSK
c. Cl$_2$, AcOH, H$_2$O or,
   (i) SO$_2$Cl$_2$
   (ii) oxidation
d. R$^Q$NH$_2$ or,
   (i) NH$_3$
   (ii) Acylation The compounds bearing R$^1$=—CH$_2$SO$_2$NHCOR$^{22}$ and —CH$_2$SO$_2$NHR$^{22}$ may be prepared as outlined in Scheme 9. The key precursor aryl-methanesulfonyl chloride 38 may be prepared by oxidation of the aryl-methylthioacetate 40 (prepared from the benzyl bromide 41 with chlorine in presence of trace amount of water [Bagnay and Dransch, Chem. Ber., 93, 784 (1960)]. Alternatively, the aryl-methylthioacetate 40 can be oxidized with sulfuryl chloride in the presence of acetic anhydride to form arylmethylsulfinyl chloride [S. Thea and G. Cevasco, Tet. Lett., 28, 5193 (1987)], which can be further oxidized with appropriate oxidizing agents to give the sulfonyl chloride 38. The compounds 42 and 43 can be obtained by reacting the sulfonyl chloride 38 with appropriate amines.

Compounds where R$^1$=—NHSO$_2$NHR$^{22}$ may be prepared by the reaction of appropriate primary amines with the sulfamide 44 [S. D. McDermott and W. J. Spillane, Synthesis, 192 (1983)], as described in Scheme 10. The compound 44 may be obtained from the corresponding N-t-butylsulfamide 45 after treatment with anhydrous trifluoroacetic acid [J. D. Catt and W. L. Matier, J. Org. Chem., 39, 566 (1974)]. The N-t-butylsulfamide 45 may be prepared by the reaction of the aromatic amine 46 with t-butylsulfamoyl chloride [W. L. Matier, W. T. Comer and D. Deitchman, J. Med. Chem., 15, 538 (1972)].

SCHEME 10

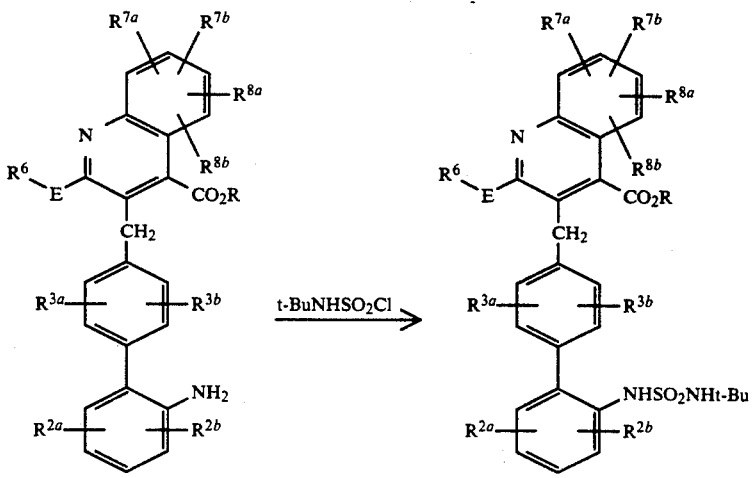

SCHEME 10
-continued

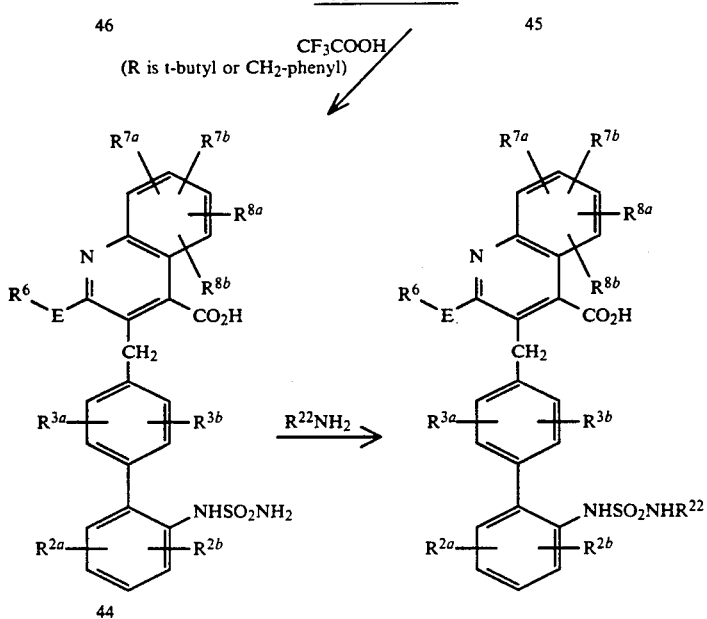

Further functionalization of compounds of Formula 1 where $R^{8a}$ or $R^{8b}$ is nitro is available through the following route (Scheme 11). The nitro group of 47 may be reduced to the amine 48 by reduction with hydrogen over palladium on carbon. The amine may then be acylated with acid chlorides to give amides under basic conditions. The acylation of the amine with chloroformates is best carried out in the presence of sodium hydride to form the anilinium anion. This anion reacts quickly with chloroformates to give the carbamates 49. The carbamate may be isolated and then deprotonated with lithium hexamethyldisilazide and alkylated to give the N,N-dialkylated carbamates 50. Alternatively this process may be carried out in one pot by first preforming the anilinium anion, acylating it and then deprotonating in situ and alkylating with $R^4$ iodide group to give 50. The amine 48 reacts slowly with isocyanates to give ureas 51. Trisubstituted ureas 52 may be prepared from the benzyl carbamate 49 ($R^{22}$=benzyl) by treatment with the magnesium salt of a secondary amine. The trisubstituted ureas may be N-alkylated by deprotonation with lithium hexamethyldisilazide and alkylation with an $R^4$ iodide to give 53. The amine may be further derivatized or converted to other groups by means of chemical procedures well known to those skilled in the art.

SCHEME 11

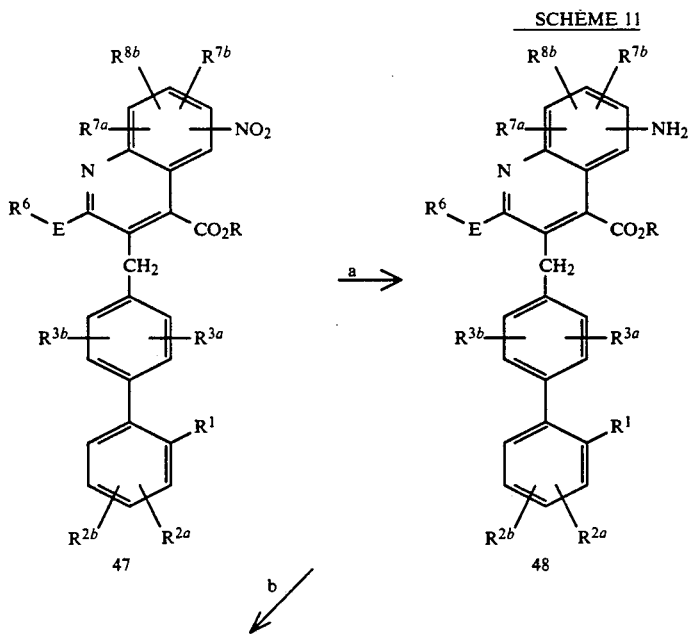

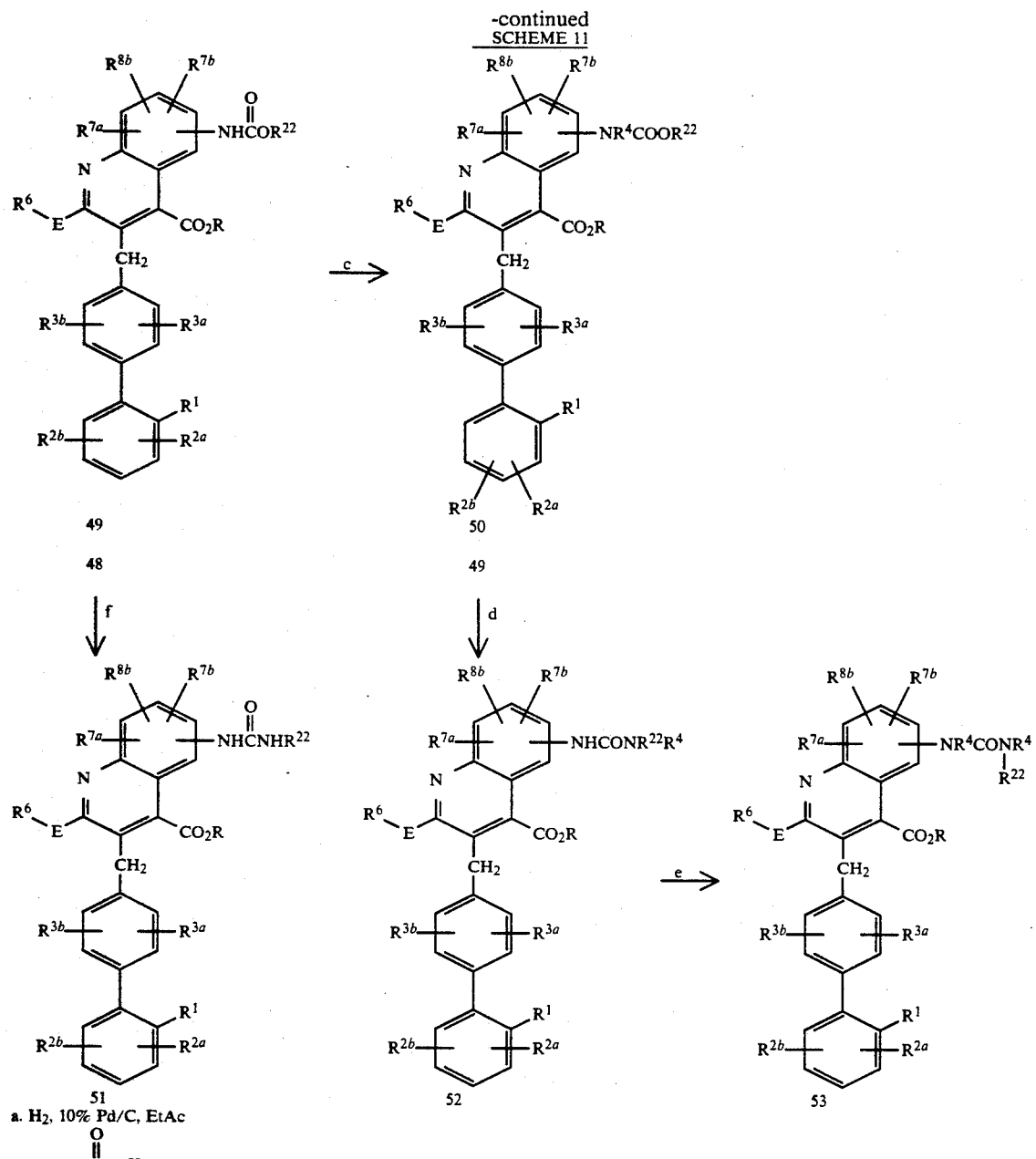

a. H₂, 10% Pd/C, EtAc
b. NaH, ClCOR²², DMF
c. LiN(TMS)₂, R⁴I
d. MeMgBr, R⁴NHR²², THF, reflux
e. LiN(TMS)₂, R⁴I, DMF
f. R²²NCO, CH₂Cl₂

It will be appreciated by those skilled in the art that the protecting groups used in these syntheses will be chosen to be compatible with subsequent reaction conditions. Ultimately, they will be removed to generate the active compounds of formula (I). For example, $R^1$ as carboxyl is often protected as its t-butyl ester which in the last step is removed by treatment with trifluoroacetic acid. Aqueous acetic acid employed overnight is a preferred method to remove a trityl protecting group to liberate an $R^1$ tetrazole group.

The compounds of this invention form salts with various inorganic and organic bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. The nontoxic, physiologically, acceptable salts are preferred, although other salts are also useful; e.g., in isolating or purifying the product.

The salts can be formed by conventional means such as by reacting the free acid forms of the product with one or more equivalents of the appropriate base in a solvent or medium in which the salt is insoluble, or in a solvent such as water which is then removed in vacuo or by freeze-drying or by exchanging the cations of an existing salt for another cation on a suitable ion exchange resin.

Angiotensin II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor Binding Assay Using Rabbit Aortae Membrane Preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitracin and the suspension was used for 100 assay tubes. Samples tested for screening were done in duplicate. To the membrane preparation (0.25 ml) there was added $^{125}I$-$Sar^1Ile^8$-angiotensin II [obtained from New England Nuclear] (10 μl; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-$Sar^1Ile^8$-angiotensin II was presented as a measure of the efficacy of such compounds as AII antagonists.

Receptor Assay Using Bovine Adrenal Cortex Preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF) (0.1 mM)]. (For screening of compounds, generally duplicates of tubes are used). To the membrane preparation (0.5 ml) there was added 3H-angiotensin II (50 mM) (10 μl) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound 3H-angiotensin II was presented as a measure of the efficacy of such compounds as AII antagonists.

The potential antihypertensive effects of the compounds described in the present invention may be evaluated using the methodology described below:

Male Charles River Sprague-Dawley rats (300-375 gm) were anesthetized with methohexital (Brevital; 50 mg/kg i.p.) and the trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volumn—1.1 cc per 100 grams body weight). The right carotid artery was ligated, both left and right vagal nerves were cut, and the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered, and 15 minutes later propranolol (1 mg/kg i.v.). Thirty minutes later angiotensin II or other agonists were administered intravenously at 30-minute intervals and the increase in the diastolic blood pressure was recorded before and after drug or vehicle administration.

Using the methodology described above, representative compounds of the invention were evaluated and were found to exhibit an activity of at least $IC_{50} < 50$ μM thereby demonstrating and confirming the utility of the compounds of the invention as effective AII antagonists.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives such as diuretics, angiotensin converting enzyme inhibitors, calcium channel blockers or β-blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methylclothiazide, methyldopa, methyldopate hydrochloride, minoxidil, pargyline hydrochloride, polythiazide, prazosin, propranolol, *rauwolfia serpentina*, rescinnamine, reserpine, sodium nitroprusside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5–250 milligrams per day range can be effectively combined at levels at the 0.5–250 milligrams per day range with the following compounds at the indicated per day dose range: hydrochlorothiazide (15–200 mg) chlorothiazide (125–2000 mg), ethacrynic acid (15–200 mg), amiloride (5–20 mg), furosemide (5–80 mg), propranolol (20–480 mg), timolol maleate (5–60 mg.), methyldopa (65–2000 mg), felodipine (5–60 mg), nifedipine (5–60 mg), and nitrendipine (5–60 mg). In addition, triple drug combinations of hydrochlorothiazide (15–200 mg) plus amiloride (5–20 mg) plus angiotensin II antagonist of this invention (3–200 mg) or hydrochlorothiazide (15–200 mg) plus timolol maleate (5–60) plus an angiotensin II antagonist of this invention (0.5–250 mg) or hydrochlorothiazide (15–200 mg) and nifedipine (5–60 mg) plus an angiotensin II antagonist of this invention (0.5–250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rate passive avoidance assay in which cholinomimetics such as physostigmine and nootropic agents are known to be active. In this assay, rats are trained to inhibit their natural tendency to enter dark areas. The test apparatus used consists of two chambers, one of which is brightly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule: in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced sterotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Perferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers and as nimodipine, and nootropic agents such as piracetam.

In order to achieve optimal anxiolytic activity, the compounds of this invention may be combined with other anxiolytic agents such as alprazolam, lorazepam, diazepam, and busipirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of formula (I) and their incorporation into pharmaceutical compositions and as such are not to be considered as limiting the invention set forth in the claims appended hereto. All $^1$H-NMR spectra were recorded on a Varian XL-200 or XL-300 Fourier transform spectrometer. Chemical shifts are reported as (parts per million) downfield from tetramethyl silane. Mass spectra were obtained from the Merck and Co. mass spectral facility in Rahway N.J. Analytical TLC was conducted on Analtec precoated silica plates (0.25 mm on glass, Silicagel-GF) with UV visualization. All reactions were carried out under an atmosphere of dry nitrogen under standard conditions for those skilled in the art.

EXAMPLE 1

Ethyl 3-cyclopropyl-3-oxopropionate

To a stirred solution of 23.8 g ethyl hydrogen malonate (180 mmoles) in 350 mL of dry THF, and cooled to −75° C. under nitrogen atmosphere, was added dropwise 145 mL of 2.5M n-butyllithium in hexane (363 mmoles), keeping the temperature below −55° C. The resultant suspension was warmed to ca. 0° C. and held at 0° to 10° C. for 20 minutes; it was then recooled to ←70° C. and cyclopropanecarbonyl chloride (10.0 mL, 11.5 g, 109 mmoles) was added dropwise. with stirring, maintaining the temperature below −60° C. It was then warmed to room temperature, diluted with 300 mL of ether, and carefully treated, with stirring, with 25 mL of concentrated hydrochloric acid in 200 mL of water. The phases were separated, the organic phase was washed once with water, and the aqueous phases were combined. The aqueous phases were extracted three times with ether, the ether phases combined, washed once with water, and combined with the original organic phase. Finally, the entire organic phase was washed once with saturated aqueous NaHCO$_3$, dried over MgSO$_4$, and the ether evaporated to give 14.9 g crude product. Distillation under reduced pressure gave 9.8 g final product, bp 88°–92° C./5 mm Hg. (Lit. 90°–95° C./4 mm Hg).

EXAMPLE 2

Ethyl 3-oxooctanoate (1)

Substituting hexanoyl chloride for cyclopropanecarbonyl chloride in Example 1 gave the title compound, bp 97°–102° C./5 mm Hg (Lit. 113°–117° C./15 mm Hg): FAB-MS: m/z 186 (M+H).

EXAMPLE 3

Ethyl 3-oxoheptanoate

Substituting valeryl chloride for cyclopropanecarbonyl chloride in Example 1 gave the title compound. Distillation (bp 92°–93° C./5 mm Hg) gave 32.4 g of product (Lit. 110°–112° C./15 mm Hg).

EXAMPLE 4

4-(2-Carboethoxy-3-oxooctyl)-2'-(2-(triphenylmethyl)-tetrazol-5-yl)biphenyl (2)

In a round-bottomed flask fitted with a nitrogen bubbler, magnetic stirring bar, and addition funnel containing 5.0 g 4-bromomethyl-2'-(2-(triphenylmethyl)tetrazol-5-yl)biphenyl (9 mmoles) in 50 mL of freshly distilled THF were placed 5.0 g ethyl 3-oxooctanoate (27 mmoles), 50 mL absolute EtOH, and 2.3 mL of a 25% solution of NaOCH$_3$ in methanol (11 mmoles). The EtOH solution was cooled to 0° C. Upon completion of the 2 hour addition of the THF solution, the reaction mixture was stirred overnight at room temperature.

The product was isolated by evaporation of the solvent, redissolved in 20 mL H$_2$O, and adjusted to pH4 using 1M KH$_2$PO$_4$. The crude product 2 was then extracted from the aqueous solution with chloroform (which had been dried over MgSO$_4$), and isolated by evaporation of the solvent, yielding 4.9 g.

EXAMPLE 5

4-(2-Carboethoxy-3-oxoheptyl)-2'-(2-(triphenylmethyl)-tetrazol-5-yl)biphenyl

Substituting ethyl 3-oxoheptanoate for ethyl 3-oxooctanoate in Example 4 gave the title compound.

EXAMPLE 6

4-(2-Carboethoxy-3-cyclopropyl-3-oxopropyl)-2'-(2-(triphenylmethyl)tetrazol-5-yl)biphenyl Substituting ethyl 3-cyclopropyl-3-oxopropionate for ethyl 3-oxooctanoate in Example 4 gave the title compound.

EXAMPLE 7

4-(2-Carboethoxy-3-oxopentyl)-2'-(2-(triphenylmethyl)-tetrazol-5-yl)biphenyl

Ethyl propionylacetate was substituted for ethyl 3-oxooctanoate in Example 4, and the crude product was taken up in ether, centrifuged free of insoluble material, and the solution concentrated to give crystals (5.2 g) which were isolated by filtration.

EXAMPLE 8

4-(2-Carboethoxy-3-oxohexyl)-2'-(2-triphenylmethyl)-tetrazol-5-yl)biphenyl

Substituting ethyl butyrylacetate for ethyl 3-oxooctanoate in Example 4 gave the title compound.

EXAMPLE 9

4-(3-oxooctyl)-2'-(tetrazol-5-yl)biphenyl (3)

To a solution of 2 (Example 4) (4.9 g, 7 mmoles) dissolved in 48 mL dioxane was added 48 mL of 10% aqueous KOH solution. The mixture was stirred overnight at reflux. After cooling, the solution was extracted with ether followed by the addition of 1M KH$_2$PO$_4$ to attain a pH4. Extraction with chloroform afforded 3 g of 3.

EXAMPLE 10

4-(3-Oxoheptyl)-2'-(tetrazol-5-yl)biphenyl

Substituting the product of Example 5 for 2 in Example 9 gave the title compound: FAB-MS: m/z 348 (M+H).

EXAMPLE 11

4-(3-Cyclopropyl-3-oxopropyl)-2'-(tetrazol-5-yl)-biphenyl

Substituting the product of Example 6 for 2 in Example 9 gave the title compound: FAB-MS: m/z 319 (M+H).

EXAMPLE 12

4-(3-Oxopentyl)-2'-(tetrazol-5-yl)biphenyl

Substituting the product of Example 7 for 2 in Example 9 gave the title compound.

EXAMPLE 13

4-(3-Oxohexyl)-2'-(tetrazol-5-yl)biphenyl

Substituting the product of Example 8 for 2 in Example 9 gave the title compound: FAB-MS: m/z 321(M+H).

EXAMPLE 14

4-Carboxy-6-methyl-2-pentyl-3[[2'-(2-(triphenylmethyl)tetrazol-5-yl)biphenyl-4-yl]methyl]quinoline;
4-Carboxy-6-methyl-3-butyl-2[2[2'-(2-(triphenylmethyl)tetrazol-5-yl)biphenyl-4-yl]ethyl]quinoline (6+7)

a. In a round-bottomed flask fitted with a nitrogen bubbler, rubber septum, magnetic stirring bar, and condenser was placed a solution of 1.5 g 5-methylisatin (10 mmoles), 15 mL EtOH and 3 (3.0 g, 10 mmoles) (Example 9). 4 mL of a 33% aqueous KOH was added dropwise, the reaction stirred for 7 days at 90° C. and was monitored by removal of 1 mL aliquots. The solvent was evaporated to dryness and 10 mL H$_2$O was added. The aqueous phase was acidified with 2.5M HCl, extracted with chloroform (which was dried over MgSO$_4$), and evaporated. The crude isomeric mixture was 4.2 g (4+5).

b. The crude isomeric mixture (4+5) was dissolved in 20 mL of a 1:10:90 solution (ammonium hydroxide:methanol:chloroform) and applied to a 200 mL chloroform packed 230–400 mesh silica gel column. To elute the desired product, the following solutions were used:

cholorform, 0.5:5:95, 1:10:90, 2:20:80, 3:30:70 (400 mL) and 5:50:50 (800 mL) (ammonium hydroxide:methanol:-chloroform). 200 mL fractions were collected with the final product appearing in fractions #14–16 (4+5).

c. In a round-bottomed flask fitted with a nitrogen bubbler, rubber septum, magnetic stirring bar, and condenser were placed 1.3 g 4+5 (2.7 mmoles), 13 mL DMF, 1.11 g triphenylmethyl chloride (4 mmoles), and 0.7 g triethylamine (5 mmoles). After 2 hours, the DMF was removed in vacuo. The resulting solid was dissolved in 10 mL $H_2O$ and adjusted to pH4 with a solution of 1M $KH_2PO_4$. The aqueous phase was then extracted with chloroform; the combined extracts were dried over $MgSO_4$ and concentrated to yield 2.6 g of crude product 6+7. Products 6+7 were pre-adsorbed onto silica gel and placed on a 300 mL chloroform packed silica gel column. The following solutions (1500 mL) were used: chloroform, 0.5:5:95 and 1:10:90 (ammonium hydroxide:methanol:chloroform). In collecting 300 mL fractions, the desired isomeric mixture was found in fractions #7–9 (1.0 g). Separation of the two isomers by preparative TLC (2:20:80) gave 1 g of 6.

EXAMPLE 15

4-Carboxy-6-methyl-2-pentyl-3[[2'-(tetrazol-5-yl)-biphenyl-4-yl]methyl]quinoline(4)

In a round-bottomed flask fitted with a nitrogen bubbler, rubber septum, magnetic stirring bar, and condenser were placed 0.275 g 6 (Example 14, Step C) dissolved in 11 mL acetic acid. The reaction flask was heated to 60° C. After 2 minutes, 5 mL $H_2O$ was added dropwise. The reaction continued for 2 hours; the solution was concentrated and purified by preparative TLC (2:20:80) to give 0.174 g of 4, which was subsequently recrystallized from EtOH. Anal. Calcd for $C_{30}H_{29}N_5O_2$. 1.5 $H_2O$.0.5 $NH_3$: C, 68.36; H, 6.41; N, 14.62. Found: C, 68.28; H, 6.12; N, 14.57: FAB-MS: m/z 491(M+H).

EXAMPLE 16

4-Carboxy-6-methyl-2-butyl-3[[2'-(2-(triphenylmethyl)-tetrazol-5-yl)biphenyl-4-yl]methyl]quinoline; 4-Carboxy-6-methyl-3-propyl-2[2[2'-(2-(triphenylmethyl)tetrazol-5-yl)biphenyl-4-yl]ethyl]quinoline Substituting the product of Example 10 for 3 in Example 14 a, b, and c gave the title compounds.

EXAMPLE 17

4-Carboxy-6-methyl-2-butyl-3[[2'-(tetrazol-5-yl)-biphenyl-4-yl]methyl]quinoline

Substituting the desired isomer of Example 16 c for 6 in Example 15 gave the title compound. Anal. Calcd for $C_{29}H_{27}N_5O_2$.0.2$H_2O$: C, 72.39; H, 5.74; N, 14.56. Found: C, 72.31; H, 5.53; N, 14.55: FAB-MS: m/z 478(M+H).

EXAMPLE 18

4-Carboxy-6-methyl-2-cyclopropyl-3[[2'-(tetrazol-5-yl)biphenyl-4-yl]methyl]quinoline Substituting the product of Example 11 for 3 in Example 14 a, and b gave the title compound. Anal. Calcd for $C_{28}H_{23}N_5O_2$.1.0 $H_2O$: C, 70.13; H, 5.26; N, 14.61. Found: C, 70.22; H, 5.16; N, 14.62: FAB-MS: m/z 462 (M+H).

EXAMPLE 19

4-Carboxy-6-methyl-2-cyclopropyl-3[2'-(2-(triphenylmethyl)tetrazol-5-yl)biphenyl-4-yl]methyl]quinoline Substituting the product of Example 18 b for the isomeric mixture 4+5 in Example 14 c gave the title compound.

EXAMPLE 20

4-Carboxy-6-methyl-2-ethyl-3[[2'-(2-(triphenylmethyl)-tetrazol-5-yl)biphenyl-4-yl]methyl]quinoline; 4-Carboxy-6-methyl-3-methyl-2[2[2'-(2-(triphenylmethyl)tetrazol-5-yl)biphenyl-4-yl]ethyl]quinoline Substituting the product of Example 12 for 3 in Example 14 a, b, and c gave the title compounds.

EXAMPLE 21

4-Carboxy-6-methyl-2-ethyl-3[[2'-(tetrazol-5-yl)-biphenyl-4-yl]methyl]quinoline

Substituting the desired isomer of Example 20 c for 6 in Example 15 gave the title compound. Anal. Calcd for $C_{27}H_{23}N_5O_2$.2.3 $H_2O$.1.2 $NH_3$: C, 63.41; H, 6.15; N, 16.98. Found: C, 63.21; H, 5.92; N, 17.05: FAB-MS: m/z 450 (M+H).

EXAMPLE 22

4-Carboxy-6-methyl-2-propyl-3[[2'-(2-(triphenylmethyl)tetrazol-5-yl)biphenyl-4-yl]methyl]quinoline; 4-Carboxy-6-methyl-3-ethyl-2[2[2'-(2-(triphenylmethyl)tetrazol-5-yl)biphenyl-4-yl]ethyl]quinoline Substituting the product of Example 13 for 3 in Example 14 a, b, and c gave the title compounds.

EXAMPLE 23

4-Carboxy-6-methyl-2-propyl-3[[2'-(tetrazol-5-yl)-biphenyl-4-yl]methyl]quinoline Substituting the desired isomer of Example 22 c for 6 in Example 15 gave the title compound. Anal. Calcd for $C_{28}H_{25}N_5O_2$.0.1 $H_2O$: C, 72.27; H, 5.46; N, 15.05. Found: C, 72.17; H, 5.61; N, 14.91: FAB-MS: m/z 464(M+H).

EXAMPLE 24

4-Carbomethoxy-6-methyl-2-pentyl-3[[2'-(2-(triphenylmethyl)tetrazol-5-yl)biphenyl-4-yl]methyl]-quinoline (8)

Product 6 (0.358 g), Example 14 was dissolved in THF and a solution of diazomethane in ether was added dropwise until the color persisted. Evaporation of the solvent and purification by preparative TLC yielded product 8 (0.250 g).

EXAMPLE 25

4-Carbomethoxy-6-methyl-2-butyl-3[[2'-(2-(triphenylmethyl)tetrazol-5-yl)biphenyl-4-yl]methyl]quinoline Substituting the desired isomer from Example 16 c for 6 in Example 24 gave the title compound.

EXAMPLE 26

4-Carbomethoxy-6-methyl-2-cyclopropyl-3[[2'-(2-(triphenylmethyl)tetrazol-5-yl)biphenyl-4-yl]-methyl]-quinoline Substituting the product from Example 19 for 6, Example 14, in Example 24 gave the title compound.

EXAMPLE 27

4-Carbomethoxy-6-methyl-2-propyl-3[[2'-(2-(triphenylmethyl)tetrazol-5-yl)biphenyl-4-yl]methyl]quinoline Substituting the desired isomer from Example 22 for 6, Example 14, in Example 24 gave the title compound.

EXAMPLE 28

4-Hydroxymethyl-6-methyl-2-pentyl-3[[2'-(2-(triphenylmethyl)tetrazol-5-yl)biphenyl-4-yl]methyl]-quinoline(9)

Product 8 (Example 24; 0.250 g; 0.340 mmoles) was dissolved in 3.5 mL of freshly distilled THF and added dropwise to 2.0 mL of 1.0M LiAlH$_4$ in ether (2 mmoles) while stirring under nitrogen in a $-15°$ C. bath. The reaction was held at this temperature for 2 hours after which it was quenched by addition to 30 mL THF containing 1 mL H$_2$O while stirring vigorously under nitrogen in an ice bath. After adding MgSO$_4$ and stirring, the mixture was filtered and evaporated to a gum, taken up in chloroform, again dried with MgSO$_4$, filtered and evaporated. Purification by preparative TLC gave 0.180 g of the desired product 9.

EXAMPLE 29

4-Hydroxymethyl-6-methyl-2-butyl-3[[2'-(2-(triphenylmethyl)tetrazol-5-yl)biphenyl-4-yl]methyl]quinoline Substituting the product of Example 25 for product 8 in Example 28 gave the title compound.

EXAMPLE 30

4-Hydroxymethyl-6-methyl-2-cyclopropyl-3[[2'-(2-(triphenylmethyl)tetrazol-5-yl)biphenyl-4-yl]methyl]-quinoline Substituting the product of Example 26 for product 8 in Example 28 gave the title compound: FAB-MS: m/z 448 (M+H).

EXAMPLE 31

4-Hydroxymethyl-6-methyl-2-propyl-3[[2'-(2-(triphenylmethyl)tetrazol-5-yl)biphenyl-4-yl]methyl]-quinoline Substituting the product of Example 27 for product 8 in Example 28 gave the title compound.

EXAMPLE 32

4-Hydroxymethyl-6-methyl-2-pentyl-3[[2'-(tetrazol-5-yl)biphenyl-4-yl]methyl]quinoline (11)

Substituting product 9 (Example 28) for 6 in Example 15 gave the title compound 11: FAB-MS: m/z 478 (M+H).

EXAMPLE 33

4-Hydroxymethyl-6-methyl-2-butyl-3[[2'-(tetrazol-5-yl)biphenyl-4-yl]methyl]quinoline Substituting the product from Example 29 for 6 in Example 15 gave the title compound. Anal. Calcd for C$_{29}$H$_{29}$N$_5$O.0.6 H$_2$O: C, 73.43; H, 6.42; N, 14.76. Found: C, 73.48; H, 6.25; N, 14.80.

EXAMPLE 34

4-Hydroxymethyl-6-methyl-2-cyclopropyl-3[[2'-(tetrazol-5-yl)biphenyl-4-yl]methyl]quinoline Substituting the product from Example 26 for 6 in Example 15 gave the title compound.

EXAMPLE 35

4-Hydroxymethyl-6-methyl-2-propyl-3[[2'-(tetrazol-5-yl)biphenyl-4-yl]methyl]quinoline Substituting the product from Example 27 for 6 in Example 15 gave the title compound. Anal. Calcd for C$_{28}$H$_{27}$N$_5$O.0.2 H$_2$O.0.4 CHCl$_3$: C, 68.10; H, 5.60; N, 13.98. Found: C, 68.05; H, 5.68; N, 13.95: FAB-MS: m/z 450 (M+H).

EXAMPLE 36

Ethyl 2-(4-bromobenzyl)-3-oxohexanoate

Substituting ethyl butyrylacetate for ethyl 3-oxooctanoate and 4-bromobenzyl bromide for 4-bromomethyl-2'-(2-(triphenylmethyl)tetrazol-5-yl)-biphenyl in Example 4 gave the title compound.

EXAMPLE 37

4-Bromo-(3'-oxohexyl)benzene

Substituting the product of Example 36 for 2 in Example 9 gave the title compound.

EXAMPLE 38

4-Carboxy-6-methyl-2-propyl-3[(4-bromobenzyl)methyl]-quinoline;
4-Carboxy-6-methyl-3-ethyl-2[2(4-bromobenzyl)ethyl]-quinoline (12+13)

Substituting 11 (Example 32) for 3 in Example 14 a, b gave the title compounds 12+13.

EXAMPLE 39

4-Carbomethoxy-6-methyl-2-propyl-3[(4-bromobenzyl)-methyl]quinoline;
4-Carbomethoxy-6-methyl-3-ethyl-2-[2-(4-bromobenzyl)ethyl]quinoline (14+15)

A: 5-Phenyl-2-triphenylmethyltetrazole (18a)

To a suspension of 5-phenyltetrazole (5 g; 34 mmole), stirring in 55 mL of acetone, was added 3.6 g of triethylamine (36 mmoles). The mixture was aged for 15 minutes after which triphenylmethylchloride (10.0 g; 36 mmoles) in 20 mL of THF was added; the temperature rose 8°–10° C. After stirring for 1 hour, 75 mL of H$_2$O was added and the mixture stirred for 1 hour. After filtration, washing with water and drying in vacuo at 70° C., 13.3 g of 18a was obtained.

B: 5-(2-Iodophenyl)-2-triphenylmethyltetrazole (18)

To a solution of 0.5 g (1.3 mmoles) of 18a in 10 mL dry THF cooled to $-20°$ C. under a nitrogen atmosphere was added dropwise with stirring 0.55 mL of 2.5M n-butyl lithium in hexane (1.4 mmoles). When addition was complete, the reaction was allowed to warm to $-10°$ C. over one hour, held there one hour, then cooled to $-78°$ C. After stirring a few minutes, 0.4 g (1.57 mmole) of I$_2$ was added all at once, and stirring continued. After 1 hour the reaction mixture was allowed to warm to ambient temperature. After removal of the solvent, the residue was partitioned between CHCl$_3$ and 1M KH$_2$PO$_4$. The aqueous phase was extracted two more times, the combined organic phases washed with sufficient aqueous $Na_2S_2O_3$ to remove excess $I_2$, dried ($MgSO_4$) and the solvent evaporated. The residue was crystallized from $CH_2Cl_2$/ether to give 0.3 g product, mp 160°-162° C. (dec). For $C_{26}H_{19}N_4I$:

Calc: C, 60.71; H, 3.72; N, 10.89. Found: C, 60.70; H, 3.86; N, 10.90.

C: Substituting 12+13 for 6 in Example 15 with isomeric separation by preparative TLC (toluene) gave the title compounds 14+15.

EXAMPLE 40

4-Carbomethoxy-6-methyl-2-propyl-3[[2'-(2-(triphenyl-methyl)tetrazol-5-yl)biphenyl-4-yl]methyl]-quinoline (17)

In a 10-mL flame dried round bottom flask fitted with a nitrogen bubbler, rubber septum, and magnetic stirring bar was placed the desired isomer 14 (0.1 g, 0.24 mmoles) and 2 mL of freshly distilled THF. The reaction flask was cooled to −78° C. (dry ice/acetone bath) and 0.310 mL 1.7M solution of t-BuLi in diethyl ether was added dropwise. 0.36 mL 1M solution of $ZnCl_2$ in diethyl ether was then added. After 1 hour, the reaction solution was canulated to a flame dried chilled flask (−78° C.) containing bis(triphenylphosphine)-nickel (II)chloride (0.0078 g, 0.012 mmoles) and 5-(2-iodophenyl)-2-triphenylmethyltetrazole (18) (0.148 g, 0.288 mmoles). The reaction was stirred in an ice bath for one hour and then allowed to stir overnight at room temperature. The solvent was evaporated; 1M $KHPO_4$ and 10 mL $H_2O$ were added to pH4; and product 17 was extracted with chloroform, dried, and evaporated.

EXAMPLE 41

4-Carbomethoxy-6-methyl-2-propyl-3[[2'-(tetrazol-5-yl)biphenyl-4-yl]methyl]quinoline (18)

Substituting 17 for 6 in Example 15 gave the title compound 18.

EXAMPLE 42

4-Hydroxymethyl-6-methyl-2-propyl-3-[[2'-(tetrazol-5-yl)biphenyl-4-yl]methyl]quinoline

A:

4-Hydroxymethyl-3-(4-bromophenylmethyl)-6-methyl-2-propylquinoline (54)

To 8.0 ml 1M $LiAlH_4$ in THF (8.0 mmoles) stirred under a nitrogen atmosphere and cooled to −35° C. was added dropwise a solution of 330 mg (0.8 mmoles) of 15 in 4 ml dry THF. The mixture was stirred for 5 minutes after which the reaction vessel was transferred to a −25° C. bath, held at that temperature for 45 minutes, allowed to warm to −20° C. over 15-20 minutes, then held there for 50 minutes. The reaction was then quenched by rapid transfer to 5 ml of THF plus 0.8 ml $H_2O$, vigorously stirred under a nitrogen atmosphere and cooled to 0° C. After 5 minutes, the solvent was evaporated and the gummy residue stirred with $CHCl_3$ and a portion of $MgSO_4$. After filtration and evaporation, the residue was chromatographed on four 8"×8"×1000μ silica gel GF plates using 1:3 EtOAc:hexane to give the desired product.

B:

4-(t-Butyldimethylsilyloxymethyl)-3-(4-bromophenyl-methyl)-6-methyl-2-propylquinoline (55)

To 50 mg (0.13 mmole) of 54 in 0.5 mL of $CH_2Cl_2$ containing 25 λ $Et_3N$ (17.5 mg; 0.17 mmole) and 10 mg DMAP (0.08 mmole) was added dropwise with stirring under a nitrogen atmosphere while cooling to 0° C., 25 mg (0.17 mmole) of t-butyldimethylsilyl chloride in 0.5 mL of $CH_2Cl_2$. After stirring overnight, the reaction mixture was washed with water, dried ($MgSO_4$) and the product isolated by preparative tlc on silica gel GF using 5% EtOAc/$CH_2Cl_2$, giving clean 55.

C:

4-(t-Butyldimethylsilyloxymethyl)-3-((2'-cyanobiphenyl-4-yl)methyl-6-methyl-2-propylquinoline (56)

Following the procedure of Example 40, but substituting 55 for 14 and 2-bromobenzonitrile for 18, and purifying the crude product by preparative tlc on silica gel GF plates with 5% EtOAc in $CH_2Cl_2$, the title compound, 56, is obtained.

D:

4-(t-Butyldimethylsilyloxymethyl)-6-methyl-2-propyl-3-[[2'-(tetrazol-5-yl)biphenyl-4-yl]-methyl]quinoline (57)

A mixture of ~20 mg (0.038 mmole) of 56 and 20 mg trimethyltin azide (0.1 mmole) in 0.4 mL toluene was heated in a nitrogen atmosphere at 110° C. for 18 hours; a second 20 mg portion of trimethyltin azide was then added and heating resumed for another 24 hours. The solvent was evaporated and the crude product applied as a suspension to a 1000μ silica gel GF plate. After developing with 10% MeOH in $CH_2Cl_2$, the desired band was isolated.

E:

4-Hydroxymethyl-6-methyl-2-propyl-3-[[2'-(tetrazol-5-yl)biphenyl-4-yl]methyl]quinoline (58)

To 10 mg of 57 in 100 λ $CHCl_3$ in a polyethylene mini-centrifuge tube was added ~0.1 ml 48% aq. HF. The two-phase mix was vigorously stirred for two hours, then evaporated to dryness under a nitrogen stream. Preparative tlc of the residue on silica gel GF with 2:20:80 $NH_4OH$:MeOH:$CHCl_3$ afforded the title compound.

In those cases in which a nitro-group is present in the starting isotin, a procedure similar to that found in U.S. Pat. No. 4,680,299 was found to be superior to the usual Pfitzinger conditions, as illustrated in the following example.

EXAMPLE 43

4-Carboxy-6-nitro-2-propyl-3-[[2'-(2-(triphenylmethyl)-tetrazol-yl)biphenyl-4-yl]methyl]quinoline A mixture of 1.0 g 5-nitroisatin (5.2 mmoles), 1.66 g 4-(3-oxohexyl)-2'-(tetrazol-5-yl)-biphenyl from Example 13 (5.2 mmoles), 0.752 mL of triethylamine (5.6 mmoles) and 10 mL of ethanol was stirred at room temperature for 1 hour. A second 0.752 ml of triethylamine was added and stirring was resumed for several days, leading finally to complete solution. The reaction mixture was concentrated to dryness, taken up in 30 mL of THF, and heated with stirring to reflux. After careful dropwise addition of 20 mL of concentrated hydrochloride acid (caution: foaming occurs), refluxing was continued overnight. The reaction mixture was then carefully concentrated to remove the bulk of the THF, cooled, and extracted with CHCl₃. After drying the extract with anhydrous MgSO₄, evaporation gave a crude mixture of the title compound and its expected isomer. Following the procedures of Example 14, but substituting this mixture in steps b and c, the pure title compound is obtained.

EXAMPLE 44

Typical Pharmaceutical Compositions Containing a Compound of the Invention

A: Dry Filled Capsules Containing 50 mg of Active Ingredient Per Capsule

| Ingredient | Amount per capsule (mg) |
| --- | --- |
| 4-Carboxy-6-methyl-2-propyl-3-[(2'-(tetrazol-5-yl)biphen-4-yl)methyl]-quinoline | 50 |
| Lactose | 149 |
| Magnesium stearate | 1 |
| Capsule (size No. 1) | 200 |

The 4-carboxy-6-methyl-2-propyl-3-[(2'-(tetrazol-5-yl)biphen-4-yl)methyl]quinoline can be reduced to a No. 60 powder and the lactose and magnesium stearate can then be passed through a No. 60 blotting cloth onto the powder. The combined ingredients can then be mixed for about 10 minutes and filled into a No. 1 dry gelatin capsule.

B: Tablet

A typical tablet would contain 4-carboxy-6-methyl-2-propyl-3-[(2'-(tetrazol-5-yl)biphen-4-yl)-methyl]quinoline (25 mg), pregelatinized starch USP (82 mg), microcrystalline cellulose (82 mg) and magnesium stearate (1 mg).

C: Combination Tablet

A typical combination tablet would contain, for example, a diuretic such as hydrochlorothiazide and consist of 4-carboxy-6-methyl-2-propyl-3-[(2'-(tetrazol-5-yl)biphen-4-yl)-methyl]quinoline (50 mg) pregelatinized starth USP (82 mg), microcrystalline cellulose (82 mg) and magnesium stearate (1 mg).

D: Suppository

Typical suppository formulations for rectal administration can contain 4-carboxy-6-methyl-2-propyl-3-[(2'-(tetrazol-5-yl)biphen-4-yl)-methyl]-quinoline (0.08-1.0 mg), disodium calcium edetate (0.25-0.5 mg), and polyethylene glycol (775-1600 mg). Other suppository formulations can be made by substituting, for example, butylated hydroxytoluene (0.04-0.08 mg) for the disodium calcium edetate and a hydrogenated vegetable oil (675-1400 mg) such as Suppocire L, Wecobee FS, Wecobee M, Witepsols, and the like, for the polyethylene glycol. Further, these suppository formulations can also include another active ingredient such as another antihypertensive and/or a diuretic and/or an angiotensin converting enzyme and/or a calcium channel blocker in pharmaceutically effective amounts as described, for example, in C above.

E: Injection

A typical injectible formulation would contain 4-carboxy-6-methyl-2-propyl-3-[(2'-(tetrazol-5-yl)biphen-4-yl)-methyl]quinoline, sodium phosphate dibasic anhydrous (11.4 mg) benzyl alcohol (0.01 ml) and water for injection (1.0 ml). Such an injectible formulation can also include a pharmaceutically effective amount of another active ingredient such as another antihypertensive and/or a diuretic and/or an angiotensin converting enzyme inhibitor and/or a calcium channel blocker.

What is claimed is:

1. A compound of formula (I):

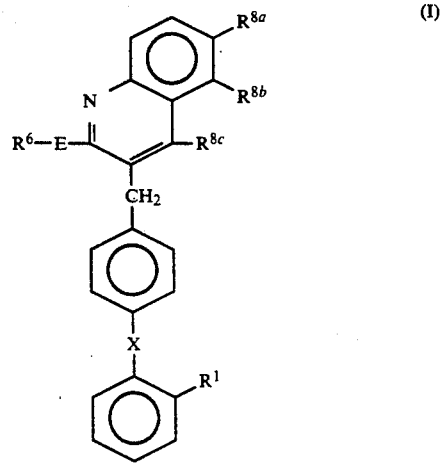

or a pharmaceutically acceptable salt thereof wherein:
$R^1$ is
  (a) -tetrazol-5-yl
E is a single bond;
$R^6$ is $C_1$–$C_6$alkyl or $C_3$–$C_7$cycloalkyl;
$R^{8a}$ is
  (a) H,
  (b) $C_1$–$C_6$alkyl,
  (c) halo,
  (d) $C_1$–$C_4$perfluoroalkyl,
  (e) —S(O)$_x$($C_1$–$C_6$ alkyl),
  (f) —NH ($C_1$–$C_6$ alkyl),
  (g) —N ($C_1$–$C_6$ alkyl)COO ($C_1$–$C_6$ alkyl),
  (h) —NO₂, or
$R^{8b}$ is $C_1$–$C_6$alkyl or hydroxy-$C_1$–$C_6$ alkyl;
$R^{8c}$ is
  (a) —CH₂COOH,
  (b) —COOH
  (c) —COO($C_1$–$C_6$ alkyl),
  (d) —CH₂OH,
  (e) —CONHSO₂($C_1$–$C_6$ alkyl),
  (f) —CONHSO₂(phenyl),
  (g) —SO₂NH(pyrid-2-yl),
  (h) —SO₂NH(perfluoro-$C_1$–$C_4$ alkyl), or
  (i) —$C_1$–$C_6$ alkyl and
X is a carbon-carbon single bond.

2. The compound of claim 1 which is:
(1) 2-Butyl-4-carboxy-3-[(2'-(tetrazol-5-yl)biphen-4-yl)methyl]quinoline;
(2) 4-Carboxy-2-propyl-3-[(2'-(tetrazol-5-yl-biphen-4-yl)methyl]quinoline;
(3) 4-Carboxy-2-ethyl-3-[(2'-(tetrazol-5-yl)-biphen-4-yl)methyl]quinoline;
(4) 4-Carboxy-2-isopropyl-3-(2'-(tetrazol-5-yl)-biphen-4-yl)methyl]quinoline;
(5) 4-Carboxy-2-cyclorpropyl-6-methyl-3-[(2'-(tetrazol-5-l)biphen-4-yl)methyl]quinoline;

(6) 4-Carboxy-6-methyl-2-propyl-3-[2'-(tetrazol-5-yl)biphen-4-yl)methyl]quinoline;
(7) 4-Carboxy-6-isopropyl-2-propyl-3-[(2'-(tetrazol-5-yl)biphen-4-yl)methyl]quinoline:
(8) 4-Carboxy-5-methyl-3-[(2'-(tetrazol-5-yl)-biphen-4-yl)methyl]quinoline;
(9) 2-Butyl-4-carboxy-6-(N-methyl-N-isopropyloxycarbonyl)amino-3-[2'-tetrazol-5-yl)biphen-4-yl)methyl]-quinoline;
(10) 4-Carboxy-6-(N-methyl)amino-2-propyl-3-[2'-(tetrazol-5-yl)biphen-4-yl)methyl]quinoline;
(11) 4-Carboxy-2-cyclopropyl-6-methylsufinyl-3-[(2'-(tetrazol-5-yl)biphen-4-yl)methyl]-quinoline;
(12) 4-Carboxy-2-ethyl-6-methylsulfonyl-3-[(2'-(tetrazol-5-yl)biphen-4-yl)methyl]quinoline;
(13) 4-Carboxy-6-(N-methyl-N-isobutyloxycarbonyl)-amino-2-propyl-3-[(2'-(tetrazol-5-yl)biphen-4-yl)methyl]quinoline;
(14) 4-Carboxy-2-propyl-6-nitro-3-[(2'-(tetrazol-5-yl)biphen-4-yl)methyl]quinoline;
(15) 4-Carboxy-2-ethyl-5-hydroxymethyl-3-[(2'-(tetrazol-5-yl)biphen-4-yl)methyl]quinoline;
(16) 4-Carboxy-2-ethyl-5-ethyl-3-[(2'-(tetrazol-5-yl)biphen-4-yl)methyl]quinoline;
(17) 4-Carboxy-2-propyl-3-[(2-(tetrazol-5-yl)-biphen-4-yl)methyl]-6-trifluoromethylquinoline;
(18) 4-Carboxy-2-ethyl-6-fluoro-3-[(2'-(tetrazol-5-yl)biphen-4-yl)methyl]quinoline;
(19) 4-Hydroxymethyl-6-methyl-2-propyl-3-[(2'-(tetrazol-5-yl)biphen-4-yl)methyl]quinoline;
(20) 4-Carbomethoxy-2-propyl-6-methyl-3[(2'-(tetrazol-5-yl)biphen-4-yl)methyl]quinoline;
(21) 4-Carboethoxy-2-ethyl-5-methyl-3-[(2'-(tetrazol-5-yl)biphen-4-yl)methyl]quinoline;
(22) 4-Carboxymethyl-6-methyl-2-propyl-3-[(2'-(tetrazol-5-yl)biphen-4-yl)methyl]quinoline;
(23) 6-Methyl-4-(N-methylsulfonyl)carboxamido-2-propyl-3-[(2'-(tetrazol-5-yl)biphen-4-yl)-methyl]quinoline;
(24) 6-Methyl-4-(N-phenylsulfonyl)carboxamido-2-propyl-3-[(2'-(tetrazol-5-yl)biphen-4-yl)-methyl]quinoline;
(25) 6-Methyl-2-propyl-4-trifluoromethanesulfonamido-3-[(2'-(tetrazol-5-yl)biphen-4-yl)-methyl]quinoline;
(26) 6-Methyl-2-propyl-4-(N-pyridin-2-yl)sulfonamido-3-[(2'-(tetrazol-5-yl)biphen-4-yl)-methyl]quinoline;
(27) 4-Carboxy-2-ethyl-6-methyl-3-[(2'-(tetrazol-5-yl)biphen-4-yl)methyl]quinoline;
(28) 2-Butyl-4-carboxy-6-methyl-3-[(2'-(tetrazol-5-yl)biphen-4-yl)methyl]quinoline;
(29) 4-Carboxy-6-methyl-2-pentyl-3-[(2'-(tetrazol-5-yl)biphen-4-yl)methyl]quinoline;
(30) 4-Hydroxymethyl-6-methyl-2-pentyl-3-[(2'-(tetrazol-5-yl)biphen-4-yl)methyl]quinoline;
(31) 2-Cyclopropyl-4-hydroxymethyl-6-methyl-3-[(2'-(tetrazol-5-yl)biphen-4-yl)methyl]quinoline;
(32) 2-Ethyl-4-hydroxymethyl-6-methyl-3-[(2'-(tetrazol-5-yl)biphen-4-yl)methyl]quinoline; and
(33) 2-Butyl-4-hydroxymethyl-6-methyl-3-[(2'-(tetrazol-5-yl)biphen-4-yl)methyl]quinoline.

3. A pharmaceutical composition useful in the treatment of hypertension which comprises a pharmaceutically acceptable carrier and a therapeutically effective amount of a compound of claim 1.

* * * * *